(12) United States Patent
Akkaraju et al.

(10) Patent No.: US 11,986,350 B2
(45) Date of Patent: May 21, 2024

(54) IMAGING DEVICES HAVING PIEZOELECTRIC TRANSDUCERS

(71) Applicant: eXo Imaging, Inc., Redwood City, CA (US)

(72) Inventors: Sandeep Akkaraju, Wellesley, MA (US); Haesung Kwon, Austin, TX (US); Yusuf Haque, Woodside, CA (US); Janusz Bryzek, Oakland, CA (US)

(73) Assignee: Exo Imaging, Inc., Santa Clara, CA (US)

( * ) Notice: Subject to any disclaimer, the term of this patent is extended or adjusted under 35 U.S.C. 154(b) by 336 days.

(21) Appl. No.: 17/237,723

(22) Filed: Apr. 22, 2021

(65) Prior Publication Data

US 2021/0236090 A1    Aug. 5, 2021

Related U.S. Application Data

(63) Continuation of application No. 15/820,319, filed on Nov. 21, 2017, now Pat. No. 11,039,814.
(Continued)

(51) Int. Cl.
*B06B 1/06* (2006.01)
*A61B 8/00* (2006.01)
(Continued)

(52) U.S. Cl.
CPC .......... *A61B 8/4494* (2013.01); *A61B 8/0883* (2013.01); *A61B 8/145* (2013.01);
(Continued)

(58) Field of Classification Search
CPC ........................... B06B 1/0238; B06B 1/0629
See application file for complete search history.

(56) References Cited

U.S. PATENT DOCUMENTS 2,808,522 A    10/1957  Dranetz
3,088,323 A     5/1963  Walter et al.
(Continued)

FOREIGN PATENT DOCUMENTS

CN       1445872 A    10/2003
CN     102577436 A     7/2012
(Continued)

OTHER PUBLICATIONS

Co-pending U.S. Appl. No. 17/215,776, inventors Bircumshaw; Brian et al., filed Mar. 29, 2021.
(Continued)

*Primary Examiner* — Bryan P Gordon
(74) *Attorney, Agent, or Firm* — Morgan, Lewis & Bockius LLP

(57) ABSTRACT

An imaging system includes: a transceiver cell for generating a pressure wave and converting an external pressure wave into an electrical signal; and a control unit for controlling an operation of the transceiver cell. The transceiver cell includes: a substrate; at least one membrane suspending from the substrate; and a plurality of transducer elements mounted on the at least one membrane. Each of the plurality of transducer elements has a bottom electrode, a piezoelectric layer on bottom electrode, and at least one top electrode on the piezoelectric layer. Each of the plurality of transducer element generates a bending moment in response to applying an electrical potential across the bottom electrode and the at least one top electrode and develops an electrical charge in response to a bending moment due to the external pressure wave.

39 Claims, 22 Drawing Sheets

Related U.S. Application Data

(60) Provisional application No. 62/433,782, filed on Dec. 13, 2016, provisional application No. 62/429,833, filed on Dec. 4, 2016, provisional application No. 62/429,832, filed on Dec. 4, 2016.

(51) Int. Cl.
| | |
|---|---|
| *A61B 8/08* | (2006.01) |
| *A61B 8/14* | (2006.01) |
| *B06B 1/02* | (2006.01) |
| *G01S 7/52* | (2006.01) |
| *G01S 7/521* | (2006.01) |
| *G01S 15/89* | (2006.01) |
| *H10N 30/00* | (2023.01) |
| *H10N 30/20* | (2023.01) |
| *H10N 30/88* | (2023.01) |

(52) U.S. Cl.
CPC .......... *A61B 8/4483* (2013.01); *A61B 8/4488* (2013.01); *A61B 8/461* (2013.01); *A61B 8/488* (2013.01); *A61B 8/5207* (2013.01); *A61B 8/546* (2013.01); *B06B 1/0215* (2013.01); *B06B 1/0238* (2013.01); *B06B 1/0629* (2013.01); *B06B 1/0662* (2013.01); *B06B 1/0692* (2013.01); *G01S 7/52046* (2013.01); *G01S 7/52079* (2013.01); *G01S 7/521* (2013.01); *G01S 15/8925* (2013.01); *H10N 30/1051* (2023.02); *H10N 30/2047* (2023.02); *H10N 30/2048* (2023.02); *H10N 30/88* (2023.02); *A61B 8/4427* (2013.01); *A61B 8/4472* (2013.01); *B06B 2201/76* (2013.01)

(56) References Cited

U.S. PATENT DOCUMENTS

| | | | |
|---|---|---|---|
| 4,156,800 A | 5/1979 | Sear et al. | |
| 4,211,949 A | 7/1980 | Brisken et al. | |
| 4,375,042 A | 2/1983 | Marcus | |
| 4,445,063 A | 4/1984 | Smith | |
| 4,517,842 A | 5/1985 | Twomey et al. | |
| 4,630,465 A | 12/1986 | Hatton | |
| 4,654,554 A | 3/1987 | Kishi | |
| 4,668,906 A | 5/1987 | Ekstrand | |
| 4,709,360 A | 11/1987 | Martin et al. | |
| 5,488,956 A | 2/1996 | Bartelt et al. | |
| 5,520,187 A | 5/1996 | Snyder | |
| 5,548,564 A | 8/1996 | Smith | |
| 5,825,117 A | 10/1998 | Ossmann et al. | |
| 5,945,770 A | 8/1999 | Hanafy | |
| 6,051,895 A | 4/2000 | Mercier | |
| 6,108,121 A | 8/2000 | Mansell et al. | |
| 7,382,635 B2 | 6/2008 | Noda | |
| 7,532,093 B1 | 5/2009 | Pulskamp et al. | |
| 8,004,158 B2 | 8/2011 | Hielscher | |
| 8,626,295 B2 | 1/2014 | Doron et al. | |
| 9,067,779 B1 | 6/2015 | Rothberg et al. | |
| 9,479,875 B2 | 10/2016 | Hall et al. | |
| 10,106,397 B1 | 10/2018 | Kim et al. | |
| 10,648,852 B2 | 5/2020 | Akkaraju et al. | |
| 10,656,007 B2 | 5/2020 | Akkaraju et al. | |
| 10,969,270 B2 | 4/2021 | Akkaraju et al. | |
| 11,039,814 B2 | 6/2021 | Akkaraju et al. | |
| 2002/0109436 A1 | 8/2002 | Peng et al. | |
| 2004/0039246 A1 | 2/2004 | Gellman et al. | |
| 2004/0085858 A1 | 5/2004 | Khuri-Yakub et al. | |
| 2005/0134574 A1 | 6/2005 | Hill | |
| 2005/0146247 A1 | 7/2005 | Fisher et al. | |
| 2005/0148132 A1 | 7/2005 | Wodnicki | |
| 2005/0200242 A1 | 9/2005 | Degertekin | |
| 2005/0203397 A1 | 9/2005 | Degertekin | |
| 2006/0113866 A1 | 6/2006 | Ganor | |
| 2007/0103697 A1 | 5/2007 | Degertekin | |
| 2007/0197922 A1 | 8/2007 | Bradley et al. | |
| 2007/0205698 A1 | 9/2007 | Chaggares et al. | |
| 2008/0009741 A1 | 1/2008 | Hyuga | |
| 2008/0048211 A1 | 2/2008 | Khuri-Yakub et al. | |
| 2009/0001853 A1 | 1/2009 | Adachi et al. | |
| 2009/0250729 A1 | 10/2009 | Lemmerhirt et al. | |
| 2010/0168583 A1 | 7/2010 | Dausch et al. | |
| 2010/0225204 A1 | 9/2010 | Hamann et al. | |
| 2010/0256501 A1 | 10/2010 | Degertekin | |
| 2010/0301227 A1 | 12/2010 | Muntean | |
| 2010/0327695 A1 | 12/2010 | Goel et al. | |
| 2011/0051461 A1 | 3/2011 | Buchwald et al. | |
| 2011/0218594 A1 | 9/2011 | Doron et al. | |
| 2012/0091543 A1 | 4/2012 | Torashima et al. | |
| 2012/0103096 A1 | 5/2012 | Kandori | |
| 2012/0127136 A1 | 5/2012 | Schneider et al. | |
| 2012/0187508 A1 | 7/2012 | Adler et al. | |
| 2012/0206014 A1 | 8/2012 | Bibl et al. | |
| 2012/0250454 A1 | 10/2012 | Rohling et al. | |
| 2012/0289897 A1 | 11/2012 | Friend et al. | |
| 2012/0319174 A1 | 12/2012 | Wang | |
| 2013/0039147 A1 | 2/2013 | Witte et al. | |
| 2013/0225993 A1* | 8/2013 | Takahashi | A61B 8/52 600/447 |
| 2013/0234559 A1 | 9/2013 | Ermolov | |
| 2013/0293065 A1 | 11/2013 | Hajati et al. | |
| 2013/0294201 A1* | 11/2013 | Hajati | G01N 29/2406 310/334 |
| 2013/0331705 A1 | 12/2013 | Fraser | |
| 2014/0019072 A1 | 1/2014 | Alles | |
| 2014/0073927 A1* | 3/2014 | Chung | H01L 29/84 600/459 |
| 2014/0117812 A1* | 5/2014 | Hajati | B06B 1/0622 310/314 |
| 2014/0145561 A1 | 5/2014 | Jin et al. | |
| 2014/0211592 A1* | 7/2014 | Miyazawa | B06B 1/0215 367/135 |
| 2014/0219063 A1 | 8/2014 | Hajati et al. | |
| 2014/0220723 A1 | 8/2014 | Liu et al. | |
| 2014/0225476 A1 | 8/2014 | Degertekin et al. | |
| 2014/0328504 A1 | 11/2014 | Stephanou et al. | |
| 2015/0097468 A1 | 4/2015 | Hajati et al. | |
| 2015/0158053 A1* | 6/2015 | Lee | H10N 30/079 156/701 |
| 2015/0187347 A1* | 7/2015 | Kojima | H10N 30/10516 310/322 |
| 2015/0250452 A1 | 9/2015 | Jin et al. | |
| 2015/0265245 A1 | 9/2015 | Von Ramm et al. | |
| 2016/0027991 A1 | 1/2016 | Suzuki | |
| 2016/0036412 A1* | 2/2016 | Suzuki | B06B 1/067 310/311 |
| 2016/0045935 A1 | 2/2016 | Yoon et al. | |
| 2016/0105748 A1 | 4/2016 | Pal et al. | |
| 2016/0107194 A1 | 4/2016 | Panchawagh et al. | |
| 2016/0136686 A1 | 5/2016 | Brock-Fisher | |
| 2016/0136687 A1* | 5/2016 | Lewis, Jr. | B06B 1/0611 29/25.35 |
| 2016/0262725 A1 | 9/2016 | Boser et al. | |
| 2017/0021391 A1 | 1/2017 | Guedes et al. | |
| 2017/0209121 A1 | 7/2017 | Davis, Sr. et al. | |
| 2017/0232474 A1 | 8/2017 | Oralkan et al. | |
| 2017/0309808 A1 | 10/2017 | Hada et al. | |
| 2017/0319180 A1 | 11/2017 | Henneken et al. | |
| 2017/0322290 A1 | 11/2017 | Ng et al. | |
| 2017/0368574 A1 | 12/2017 | Sammoura et al. | |
| 2018/0153510 A1 | 6/2018 | Haque et al. | |
| 2019/0176193 A1 | 6/2019 | Shulepov et al. | |
| 2019/0316957 A1 | 10/2019 | Akkaraju et al. | |
| 2019/0316958 A1 | 10/2019 | Akkaraju et al. | |
| 2020/0205776 A1 | 7/2020 | Dekker et al. | |
| 2020/0249079 A1 | 8/2020 | Akkaraju et al. | |
| 2020/0266798 A1 | 8/2020 | Shelton et al. | |
| 2021/0069748 A1 | 3/2021 | Bircumshaw et al. | |
| 2021/0078042 A1 | 3/2021 | Bircumshaw et al. | |
| 2021/0151661 A1 | 5/2021 | Kwon et al. | |
| 2021/0172788 A1 | 6/2021 | Akkaraju et al. | |

(56) References Cited

U.S. PATENT DOCUMENTS

| | | |
|---|---|---|
| 2021/0364348 A1 | 11/2021 | Akkaraju et al. |
| 2022/0193722 A1 | 6/2022 | Bircumshaw et al. |
| 2022/0205836 A1 | 6/2022 | Akkaraju et al. |

FOREIGN PATENT DOCUMENTS

| | | |
|---|---|---|
| CN | 104271266 A | 1/2015 |
| CN | 105310718 A | 2/2016 |
| CN | 106500824 A | 3/2017 |
| CN | 106999163 A | 8/2017 |
| EP | 3453056 A1 | 3/2019 |
| JP | S61223683 A | 10/1986 |
| JP | S6276392 A | 4/1987 |
| JP | H02218983 A | 8/1990 |
| JP | H06350155 A | 12/1994 |
| JP | 2006075425 A | 3/2006 |
| JP | 2007088805 A | 4/2007 |
| JP | 2007510324 A | 4/2007 |
| JP | 2008510324 A | 4/2008 |
| JP | 2009165212 A | 7/2009 |
| JP | 2012129662 A | 7/2012 |
| JP | 2013123150 A | 6/2013 |
| JP | 2014000122 A | 1/2014 |
| JP | 2014127921 A | 7/2014 |
| JP | 2015521409 A | 7/2015 |
| JP | 2016503312 A | 2/2016 |
| JP | 2016533825 A | 11/2016 |
| JP | 2018502467 A | 1/2018 |
| JP | 2018046512 A | 3/2018 |
| KR | 1020150005960 A | 1/2015 |
| WO | WO2005120355 A1 | 12/2005 |
| WO | WO-2006123300 A2 | 11/2006 |
| WO | WO-2007099696 A1 | 9/2007 |
| WO | WO2010100861 A1 | 9/2010 |
| WO | WO-2011026187 A1 | 3/2011 |
| WO | WO-2011033887 A1 | 3/2011 |
| WO | WO-2012117996 A1 | 9/2012 |
| WO | WO-2013043906 A1 | 3/2013 |
| WO | WO-2013158348 A1 | 10/2013 |
| WO | WO2014066006 A1 | 5/2014 |
| WO | WO-2015131083 A1 | 9/2015 |
| WO | WO-2017025438 A1 | 2/2017 |
| WO | WO-2017132517 A1 | 8/2017 |
| WO | WO-2017182344 A1 | 10/2017 |
| WO | WO-2017216139 A1 | 12/2017 |
| WO | WO-2018102223 A1 | 6/2018 |
| WO | WO-2019164721 A1 | 8/2019 |
| WO | WO-2019199397 A1 | 10/2019 |
| WO | WO-2019199398 A1 | 10/2019 |
| WO | WO-2019226547 A1 | 11/2019 |
| WO | WO-2020028580 A1 | 2/2020 |
| WO | WO-2021050853 A1 | 3/2021 |

OTHER PUBLICATIONS

Co-pending U.S. Appl. No. 17/218,656, inventors Kwon; Haesung et al., filed Mar. 31, 2021.
Co-pending U.S. Appl. No. 17/364,381, inventors Mantravadi; Naresh et al., filed Jun. 30, 2021.
Co-pending U.S. Appl. No. 17/364,397, inventors Kwon; Haesung et al., filed Jun. 30, 2021.
Hill et al. The Role Radius of Curvature Plays in Thiolated Oligonucleotide Loading on Gold Nanoparticles. ACS Nano 3(2):418-424 (2009) Retrieved on Sep. 2, 2021 from https://www.ncbi.nlm.nih.gov/pmc/articles/PMC3241534.
PCT/US2021/039977 International Search Report and Written Opinion dated Oct. 6, 2021.
PCT/US2021/039994 International Search Report and Written Opinion dated Nov. 5, 2021.
APC International, Ceramic manufacturing series—poling PZT ceramics. https://www.americanpiezo.com/blog/ceramic-manufacturing-series-poling-pzt-ceramics/ [1-3] (2016).
Assef et al., A reconfigurable arbitrary waveform generator using PWM modulation for ultrasound research. BioMedical Engineering OnLine 12:24 [1-13] (2013).
Choudhry et al., Comparison of tissue harmonic imaging with conventional US in abdominal disease. RadioGraphics: Imaging and Therapeutic Technology 20:1127-1135 (2000).
Dahl, Ultrasound beamforming and image formation. http://people.duke.edu/-jjd/RSNA_USbeamforming.pdf [Slide presentation] (c. 2005).
Dausch et al., Theory and operation of 2-D array piezoelectric micromachined ultrasound transducers. IEEE Transactions on Ultrasonics, Ferroelectrics, and Frequency Control 55(11):2484-2492 (2008).
Doerry, Generating nonlinear FM chirp waveforms for radar. Sandia Report, SAND2006-5856:1-34 (2006).
Felix et al., Biplane ultrasound arrays with integrated multiplexing solution for enhanced diagnostic accuracy in endorectal and transvaginal imaging. http://www.vermon.com/vermon/publications/Felix_UFFC_2005.pdf (2005).
Goldman, Apple's Lightning connector and you: what you should know. CNET Sep. 19, 2012: https://www.cnet.com/news/apples-lightning-connector-and-you-what-you-should-know/ (2012).
Guedes et al., Aluminum nitride pMUT based on a flexurally-suspended membrane. IEEE 16th International Solid-State Sensors, Actuators and Microsystems Conference:12169346 (2011).
Hajati et al., Three-dimensional micro electromechanical system piezoelectric ultrasound transducer. Appl. Phys. Lett. 101:253101 (2012).
Harput, Use of chirps in medical ultrasound imaging. Ultrasound Group, School of Electronic and Electrical Engineering, University Of Leeds, PHD Thesis, Dec. 2012.
Karki, Signal conditioning piezoelectric sensors. Texas Instruments Application report, SLA033A:1-5 (2000).
Khuri-Yakub et al., Capacitive micro machined ultrasonic transducers for medical imaging and therapy. Journal of Micromech Microeng. 21(5):054004-054014 (2011).
Lach et al., Piezoelectric materials for ultrasonic probes. http://www.ndt.net/article/platte2/platte2.htm NDTnet 1(9):1-9 (1996).
Lee et al., Wafer-to-wafer alignment for three-dimensional integration: a review. Journal of MicroElectroMechanical Systems 20(4):885-898 (2011).
Lu et al., High frequency piezoelectric micromachined ultrasonic transducer array for intravascular ultrasound imaging. Proceedings of the IEEE International Conference on Micro Electro Mechanical Systems (MEMS):06765748 (2014).
Martin, Introduction to B-mode imaging. Cambridge University Press; Diagnostic Ultrasound: Physics and equipment, 2nd Edition. Chapter 1:1-10 (2010).
Mina, High frequency transducers from PZT films. Materials Science and Engineering Thesis; Pennsylvania State University:1-199 (2007).
Moazzami et al., Electrical characteristics of ferroelectric PZT thin films for DRAM applications. IEEE Transaction on Electron Devices 39(9):2044-2049 (1992).
Orenstein Scanning in pain—sonographers seek relief from job-related hazard. Radiology Today 10(8):24 (2009).
Ovland, Coherent plane-wave compounding in medical ultrasound imaging. NTNU-Trondheim, Norwegian University of Science and Technology, Master of Science Thesis, 1-62 (Jun. 2012).
PCT/US2017/063163 International Search Report and Written Opinion dated Feb. 15, 2018.
PCT/US2019/021501 International Search Report and Written Opinion dated Jul. 12, 2019.
PCT/US2019/021515 International Search Report and Written Opinion dated May 31, 2019.
PCT/US2019/033119 International Search Report and Written Opinion dated Aug. 9, 2019.
PCT/US2019/044528 International Search Report and Written Opinion dated Oct. 16, 2019.
PCT/US2020/050374 International Search Report and Written Opinion dated Feb. 2, 2021.
PCT/US2020/050374 Invitation to Pay Additional Fees dated Nov. 13, 2020.

(56) References Cited

OTHER PUBLICATIONS

PCT/US2021/024667 International Search Report and Written Opinion dated Jul. 8, 2021.
PCT/US2021/025109 International Search Report and Written Opinion dated Jul. 7, 2021.
Pye et al., Adaptive time gain compensation for ultrasonic imaging. Ultrasound in Medicine and Biology 18(2):205-212 [abstract] (1992).
Rodriguez et al., Low cost matching network for ultrasonic transducers. Physics Procedia 3:1025-1031 (2010).
Smyth, Design and modeling of a PZT thin film based piezoelectric micromachined ultrasonic transducer (PMUT). MSME Thesis, MIT:1-156 (2012).
Spectral doppler. http://www.echocardiographer.org/Echo%20Physics/spectral%20doppler.html (2017).
Szabo. Diagnostic ultrasound imaging: inside out. Elsevier Academic Press, ISBN: 0-12-680145-2 (572 pgs) (2014).
Trots et al., Synthetic aperture method in ultrasound imaging. InTech Press; Ultrasound Imaging, Masayuki Tanabe (Ed.). http://www.intechopen.com/books/ultrasound-imaging/synthetic-aperture-method-in-ultrasound-imaging. Chapter 3:37-56 (2011).

U.S. Appl. No. 15/820,319 Office Action dated May 14, 2020.
U.S. Appl. No. 15/951,118 Office Action dated Sep. 20, 2019.
U.S. Serial No. 15/951,121 Office Action dated May 6, 2019.
U.S. Appl. No. 15/951,121 Office Action dated Nov. 19, 2019.
U.S. Appl. No. 16/833,333 Office Action dated Sep. 8, 2020.
U.S. Appl. No. 16/837,800 Office Action dated May 7, 2021.
Wang et al., Broadband piezoelectric micromachined ultrasonic transducer (pMUT) using mode-merged design. Proceedings of the 10th IEEE International Conference on Nano/Micro Engineered and Molecular Systems (IEEE-NEMS 2015):15260900. Xi'an, China, Apr. 7-11, 2015.
Wang et al., Zero-bending piezoelectric micromachined ultrasonic transducer (pMUT) with enhanced transmitting performance. Journal of Microelectromechanical Systems 24(6):2083-2091 (2015).
Zhang et al. Double-SOI wafer-bonded CMUTs with improved electrical safety and minimal roughness of dielectric and electrode surfaces. Journal of microelectromechanical systems 21(3):668-680 (2012).
U.S. Appl. No. 17/180,308 Office Action dated Dec. 10, 2021.
Extended European Search Report for Application No. EP22199284.5, dated May 2, 2023, 8 pages.

* cited by examiner

IMAGING DEVICES HAVING PIEZOELECTRIC TRANSDUCERS

CROSS-REFERENCE

This application is a continuation application of U.S. Ser. No. 15/820,319, filed Nov. 21, 2017, which claims the benefit of U.S. Provisional Application No. 62/433,782, filed Dec. 13, 2016, entitled "Micromachined Transceiver Array," U.S. Provisional Application No. 62/429,832, filed Dec. 4, 2016, entitled "A Configurable Ultrasonic Line Imager," and U.S. Provisional Application No. 62/429,833, filed Dec. 4, 2016, entitled "Low Voltage, Low Power MEMS Transducer with Direct Interconnect," which are hereby incorporated by reference in their entirety.

BACKGROUND

Technical Field

The present invention relates to imaging devices, and more particularly, to imaging devices having piezoelectric transducers.

Background of the Invention

A non-intrusive imaging system for imaging internal organs of a human body and displaying images of the internal organs transmits signals into the human body and receives signals reflected from the organ. Typically, transducers that are used in an imaging system are referred to as transceivers and some of the transceivers are based on photo-acoustic or ultrasonic effects. In general, piezoelectric transducers are used for imaging as well as other applications, such as medical imaging, flow measurements in pipes, speaker, microphone, lithotripsy, heating tissue for therapeutics, and highly intensive focused ultrasound (HIFU) for surgery.

Advances in micro-machining technologies allow sensors and actuators to be efficiently incorporated on a substrate. In particular, micromachined ultrasound transducers (MUTs), using capacitive transduction (cMUTs) or piezoelectric transduction (pMUTs), are particularly advantageous compared to the conventional bulk piezoelectric elements having a large form factor. Although the basic concepts for these transducers have been disclosed in the early 1990's, commercial implementation of these concepts has met with a number of challenges. For instance, the conventional cMUT sensors are particularly prone to failure or drift in performance due to the dielectric charge build-up during operation. The conventional pMUTs have been a promising alternative but have issues related to transmission and receive inefficiencies. As such, there is a need for pMUTs that have enhanced efficiencies and can be applied to various sensing devices.

SUMMARY OF THE DISCLOSURE

In embodiments, a transceiver element includes: a substrate; at least one membrane suspending from the substrate; and a plurality of transducer elements mounted on the at least one membrane, each of the plurality of transducer elements having a bottom electrode, a piezoelectric layer on bottom electrode, and at least one top electrode on the piezoelectric layer, each of the plurality of transducer element generating a bending moment in response to applying an electrical potential across the bottom electrode and the at least one top electrode and developing an electrical charge in response to applying a bending moment thereto.

In embodiments, an imaging system includes: a transceiver cell for generating a pressure wave and converting an external pressure wave into an electrical signal; and a control unit for controlling an operation of the transceiver cell. The transceiver cell includes: a substrate; at least one membrane suspending from the substrate; and a plurality of transducer elements mounted on the at least one membrane, each of the plurality of transducer elements having a bottom electrode, a piezoelectric layer on bottom electrode, and at least one top electrode on the piezoelectric layer, each of the plurality of transducer element generating a bending moment in response to applying an electrical potential across the bottom electrode and the at least one top electrode and developing an electrical charge in response to a bending moment due to the external pressure wave.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

Figure (or "FIG.") 1 shows an imaging system according to embodiments of the present disclosure.

DETAILED DESCRIPTION OF THE PREFERRED EMBODIMENTS

In the following description, for purposes of explanation, specific details are set forth in order to provide an understanding of the disclosure. It will be apparent, however, to one skilled in the art that the disclosure can be practiced without these details. Furthermore, one skilled in the art will recognize that embodiments of the present disclosure, described below, may be implemented in a variety of ways, such as a process, an apparatus, a system, or a device.

Elements/components shown in diagrams are illustrative of exemplary embodiments of the disclosure and are meant to avoid obscuring the disclosure. Reference in the specification to "one embodiment," "preferred embodiment," "an embodiment," or "embodiments" means that a particular feature, structure, characteristic, or function described in connection with the embodiment is included in at least one embodiment of the disclosure and may be in more than one embodiment. The appearances of the phrases "in one embodiment," "in an embodiment," or "in embodiments" in various places in the specification are not necessarily all referring to the same embodiment or embodiments. The terms "include," "including," "comprise," and "comprising" shall be understood to be open terms and any lists that follow are examples and not meant to be limited to the listed items. Any headings used herein are for organizational purposes only and shall not be used to limit the scope of the description or the claims. Furthermore, the use of certain terms in various places in the specification is for illustration and should not be construed as limiting.

Figure 1:
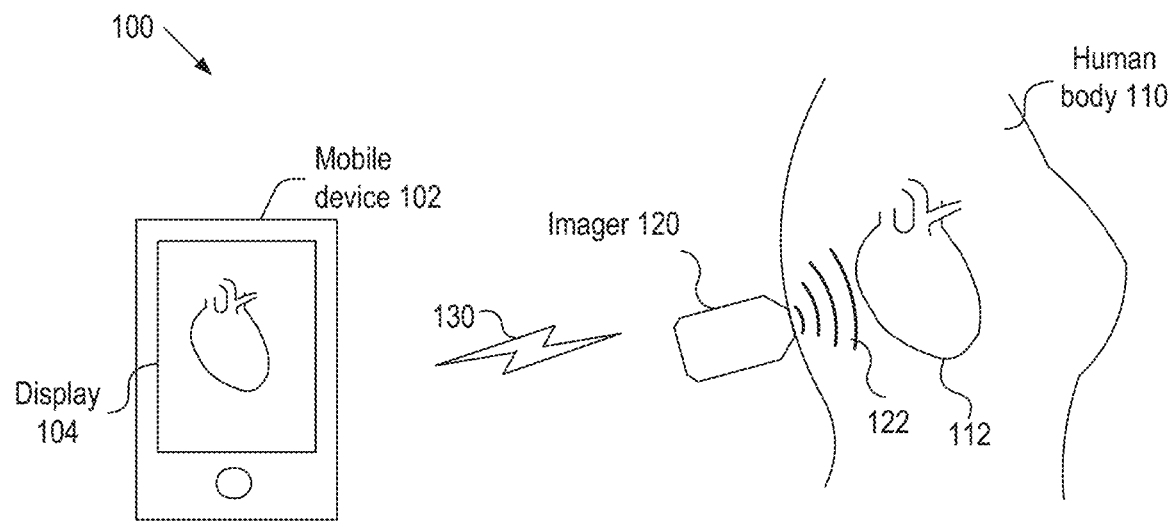

FIG. 1 shows an imaging system 100 according to embodiments of the present disclosure. As depicted, the system 100 may include: an imager 120 that generates and transmit pressure waves 122 toward an internal organ 112, such as heart, in a transmit mode/process; and a device 102 that communicates signals to the imager through a communication channel 130. In embodiments, the internal organ 112 may reflect a portion of the pressure waves 122 toward the imager 120, and the imager 120 may capture the reflected pressure waves and generate electrical signals in a receive mode/process. The imager 120 may communicate the electrical signals to the device 102 and the device 102 may display images of the human organ on a display/screen 104 using the electrical signals.

It is noted that the imager 120 may be used to get an image of internal organs of an animal, too. It is also noted that the pressure wave 122 may be acoustic, ultrasonic, or photoacoustic waves that can travel through the human/animal body and be reflected by the internal organs.

In embodiments, the imager 120 may be a portable device and communicate signals through the communication channel 130, either wirelessly or via a cable, with the device 102. In embodiments, the device 102 may be a mobile device, such as cell phone or iPad, or a stationary computing device that can display images to a user.

Figure 2:
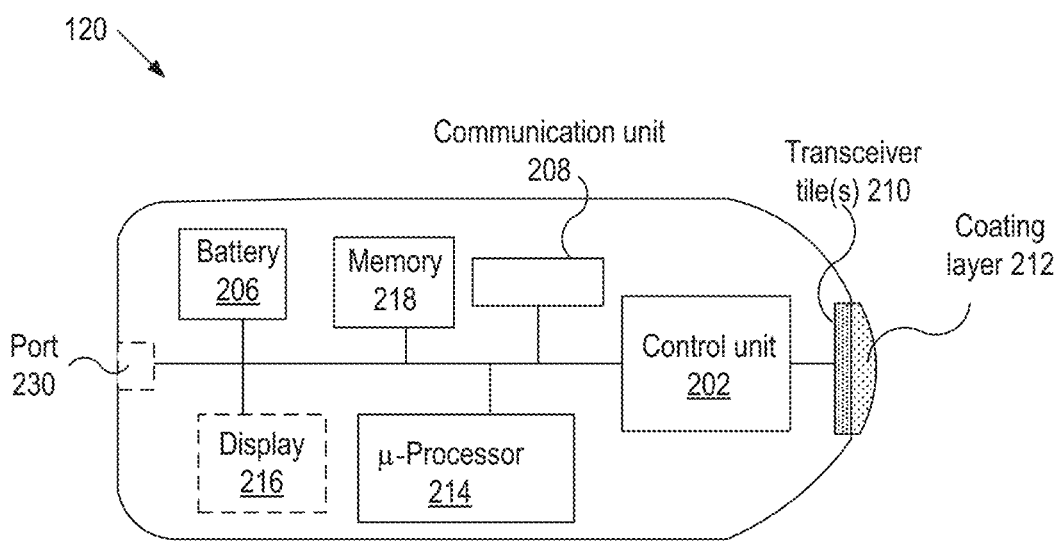
FIG. 2 shows a block diagram of an imager according to embodiments of the present disclosure.

FIG. 2 shows a block diagram of the imager 120 according to embodiments of the present disclosure. In embodiments, the imager 120 may be an ultrasonic imager. As depicted in FIG. 2, the imager 120 may include: a transceiver tile(s) 210 for transmitting and receiving pressure waves; a coating layer 212 that operates as a lens for focusing the pressure waves and also functions as an impedance interface between the transceiver tile and the human body 110; a control unit 202, such as ASIC chip, for controlling the transceiver tile(s) 210; a microprocessor 214 for controlling the components of the imager 120; a communication unit 208 for communicating data with an external device, such as the device 102, through one or more ports 230; a memory 218 for storing data; a battery 206 for providing electrical power to the components of the imager; and optionally a display 216 for displaying images of the target organs.

In embodiments, the device 102 may have a display/screen. In such a case, the display may not be included in the imager 120. In embodiments, the imager 120 may receive electrical power from the device 102 through one of the ports 230. In such a case, the imager 120 may not include the battery 206. It is noted that one or more of the components of the imager 120 may be combined into one integral electrical element. Likewise, each component of the imager 120 may be implemented in one or more electrical elements.

In embodiments, the user may apply gel on the coating layer 212 so that the impedance matching between the coating layer 212 and the human body 110 may be improved, i.e., the power loss at the interface is reduced.

Figure 3A:
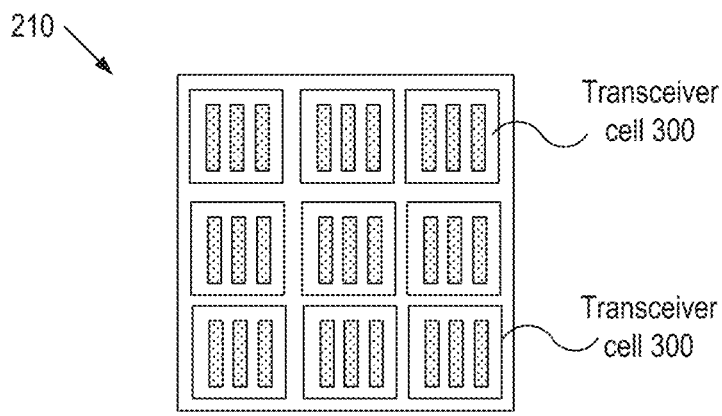
FIG. 3A shows a schematic diagram of an exemplary transceiver tile according to embodiments of the present disclosure.

FIG. 3A shows a schematic diagram of an exemplary transceiver tile 210 according to embodiments of the present disclosure. While the number of cells 300 and the arrangement of the transceiver cells within the transceiver tile 210 can be arbitrary in nature, some typical arrangements may include a rectangular grid, hexagonal grid, annular grid, polar grid and so on. Purely for illustrative purposes, the transceiver tile 210 having nine transceiver cells 300 is shown in FIG. 3A.

Figure 3B:
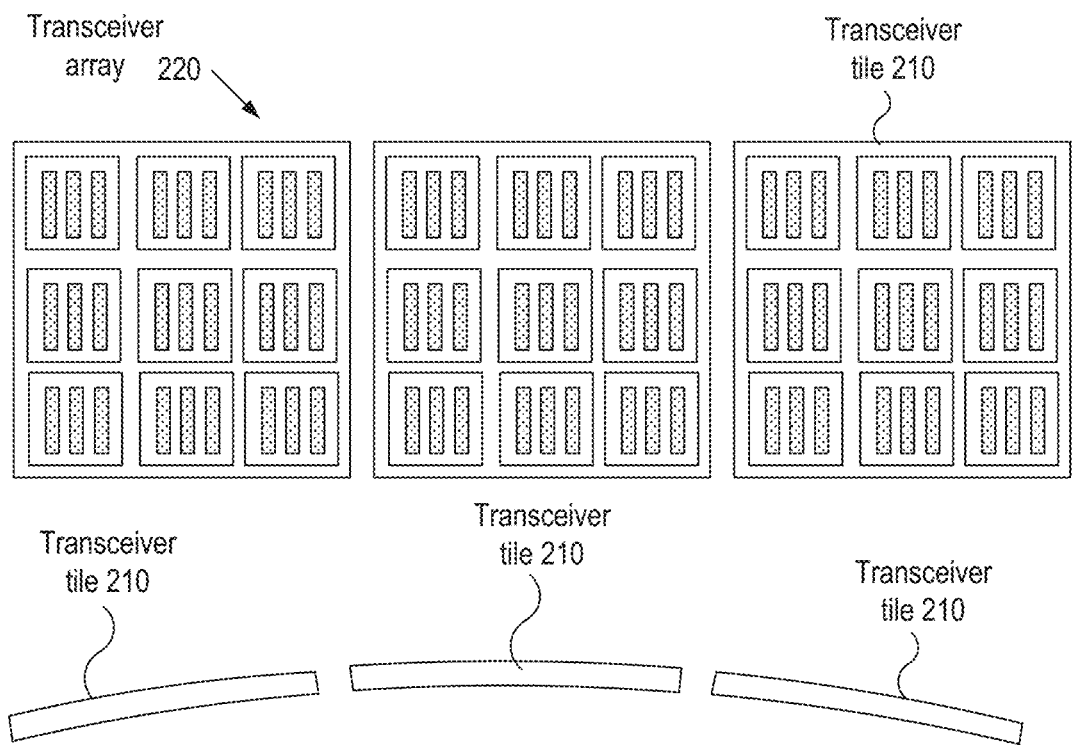
FIG. 3B shows top and side views of a transceiver array that includes one or more transceiver tiles according to embodiments of the present disclosure.

FIG. 3B shows top and side views of a transceiver array 220 that includes one or more transceiver tiles according to embodiments of the present disclosure. As depicted, the transceiver array 220 may include one or more transceiver tiles 210 arranged in a predetermined manner. For instance, the transceiver tiles (or, shortly tiles) 210 may be physically bent to further form a curved transceiver array and disposed in the imager 120. It should be apparent to those of ordinary skill in the art that the imager 112 may include any suitable number of tiles and the tiles may be arranged in any suitable manner, and each tile 210 may include any suitable number of transceiver cells that are the same as or similar to the cell 300. In embodiments, the transceiver array 220 may be a micro-machined array fabricated from a substrate.

Figure 4A:
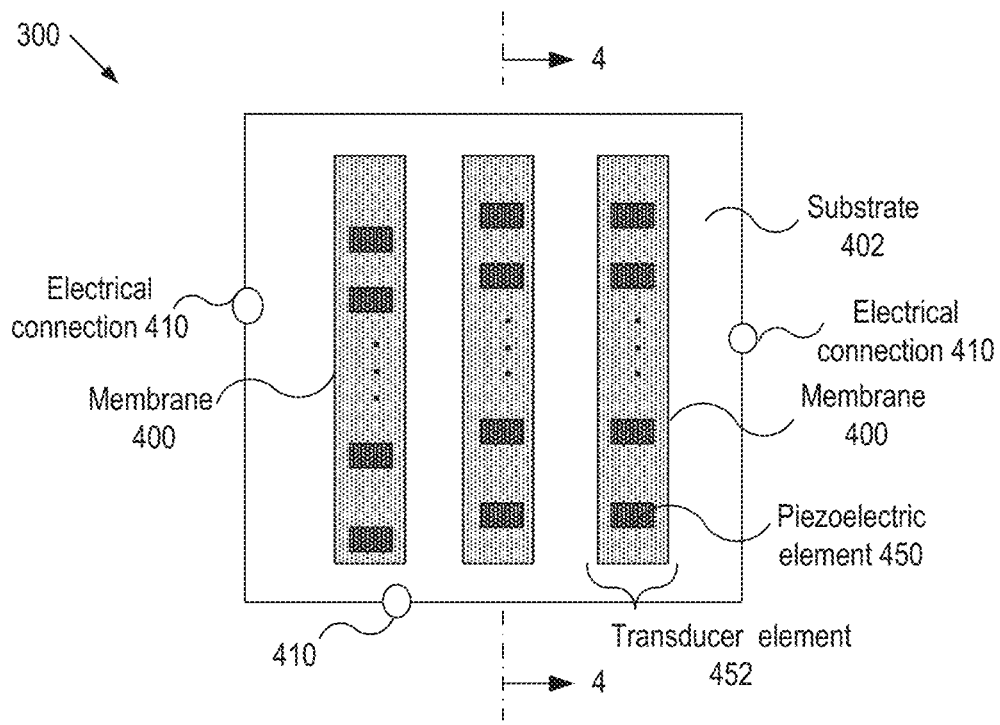
FIG. 4A shows an enlarged view of a transceiver cell according to embodiments of the present disclosure.

FIG. 4A shows an enlarged view of the transceiver cell 300 according to embodiments of the present disclosure. As depicted, each cell includes one or more arbitrarily shaped membranes 400. Three membranes in FIG. 4A are shown purely for the purpose of illustration, even though other suitable number of membranes may be included in the transceiver cell 300. In embodiments, the transceiver cell 300 can be of any arbitrary geometrical shape, such as (but not limited to) rectangle, rhomboid, hexagon or circle.

In embodiments, one or more piezoelectric elements 450 may be mounted on each membrane 400, where the membrane may be actuated by the piezoelectric elements 450 or by an external pressure. In embodiments, a combination of a membrane 400 and one or more piezoelectric elements 450 may be used to create a piezoelectric transducer that transmits ultrasound or acoustic waves and convert acoustic or ultrasound waves impinging on the membrane to electrical signals. In embodiments, each membrane 400 can be of arbitrary shape and can have different length, width and variable thickness.

In embodiments, each membrane 400 may be actuated at one or more primary modes of vibration. The resonance frequency of the membrane may be determined by various parameters: physical geometry of the membrane, variation of the thickness of the membrane, etc. In embodiments, the variation in the thickness of the membrane 400 may be achieved by at least one of etching the membrane and selectively depositing materials on the membrane.

In embodiments, the actuation of the membranes 400 by the piezoelectric elements 450 to create an acoustic output, i.e., pressure wave, is known as a transmit mode/process and denoted by Tx. Similarly the transduction of an external pressure on the membrane to a change in charge on the piezoelectric element is known as a receive mode/process and denoted by Rx. Hereinafter, the combination of the membrane 400 with the piezoelectric elements 450 is referred to as a transducer element 452. In embodiments, the membrane 400 may be interpreted as mechanically resonating elements including, but not limited to cantilevers, simply supported beams, diaphragms, corrugated diaphragms, and other simply supported or encastered apparatus.

In embodiments, one or more electrical connections 410 may be made to the piezoelectric elements 450 by means of electrical wires. The electrical wires (not shown in FIG. 4A) may be deposited on the transceiver cell 300 by various techniques, such as micro-machining, wire bonding techniques, or connecting external electrical circuits to the cell via vertical interconnections.

Figure 4B:
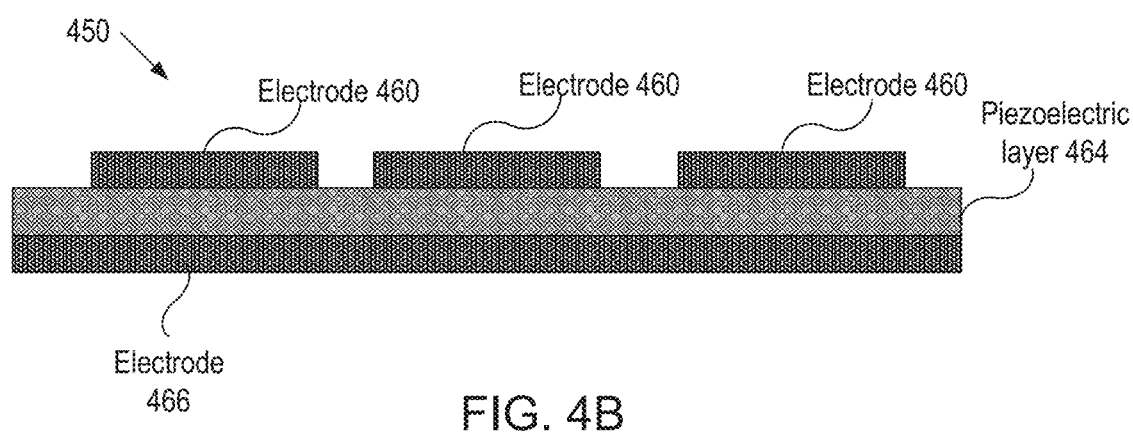
FIG. 4B shows a cross sectional view of an exemplary piezoelectric element according to embodiments of the present disclosure.

FIG. 4B shows a cross sectional view of an exemplary piezoelectric element 450 according to embodiments of the present disclosure. As depicted, the piezoelectric element 450 may include: a bottom electrode 466, one or more top electrodes 460, and a piezoelectric layer 464 disposed between the top and bottom electrodes. While a unimorph piezoelectric element is shown in FIG. 4B purely for the purpose of illustration, in embodiments, a multi-layer piezoelectric element (multi-morph) composed of a plurality of piezoelectric sublayers and electrodes can be utilized. Also, in embodiments, the piezoelectric element 450 may include one or more top electrodes, even though FIG. 4B shows three top electrodes for the purpose of illustration. In embodiments, the piezoelectric layer 464 may include at least one of PZT, KNN, PZT-N, PMN-Pt, AlN, Sc—AlN, ZnO, PVDF, and LiNiO$_3$.

In embodiments, the thickness of the piezoelectric layer 464 may be less than 100 μm and the electrical potential between the top and bottom electrodes in the Tx mode/process may be 1~20 V. In contrast, the electrical potential between the top and bottom electrodes of a conventional piezoelectric element ranges 100~200 V. Since the electrical power for driving the piezoelectric element 450 may be proportional to the square of voltage of the pulse or waveform driving the piezoelectric element, the power consumed by the piezoelectric element 450 may be significantly lower than the power consumed by the conventional piezoelectric element.

In embodiments, the piezoelectric element 450 may be a piezoelectric micromachined ultrasound transducer and fabricated by conventional techniques that are used in the semiconductor, MEMS or ultrasonic industry. Similarly, in embodiments, the other components in the transceiver array 220 may be fabricated by the conventional techniques in the semiconductor, MEMS or ultrasonic industry.

Figure 5:
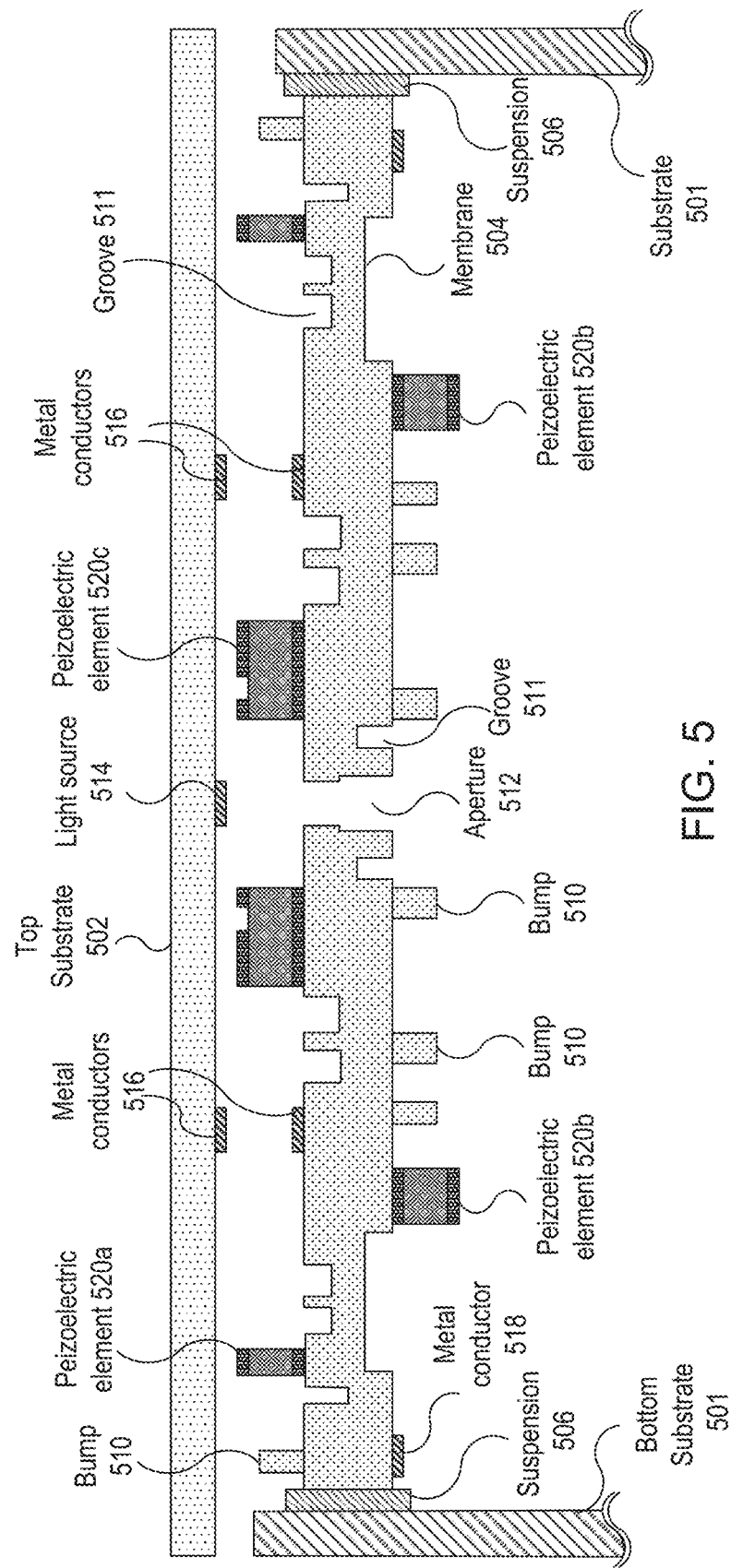
FIG. 5 shows a cross sectional view of the transceiver cell in FIG. 4A, taken along the line 4-4, according to embodiments of the present disclosure.

FIG. 5 shows a cross sectional view of the transceiver cell 300 in FIG. 4A, taken along the line 4-4, according to embodiments of the present disclosure. As depicted, the membrane 504, which may be the same as or similar to the membrane 400, may have a varying thickness and be coupled with multiple piezoelectric elements 520a-520c. In embodiments, the membrane 504 may suspend from the bottom substrate 501 (which may be the same as similar to the substrate 402 in FIG. 4A) by a suspension mechanism 506.

In embodiments, the thickness of the membrane 504 may be varied by forming one or more of grooves 511, corrugations and perforation/aperture 512 in a planar membrane. In embodiments, the thickness of the membrane 504 may be varied by forming only grooves and/or corrugations 511 in a planar membrane so that one or more hermetic cavities may be formed underneath the membrane. In embodiments, materials may be selectively deposited or deposited and patterned to form bumps 510 on the top and/or bottom surface of the membrane, where the bumps vary the thickness of the membrane. In embodiments, the thickness variation of the membrane 504 may be achieved by conventional wafer processing techniques, such as etching and deposition techniques.

In embodiments, one or more piezoelectric elements 520a-520c may be disposed on the top and/or bottom surface of the membrane 504. In embodiments, each of the piezoelectric elements 520a-520c may have two or more terminals and have different sizes and geometries. For instance, the piezoelectric element 520a and 520b may have two terminals, while the piezoelectric element 520c may have three terminals (one bottom electrode and two top electrodes).

In embodiments, the piezoelectric elements 520a-520c may be connected to electrical wires/conductors (now shown in FIG. 5), where the electrical wires may be deposited on the membrane 504 by various techniques, such as micro-machining, patterning, wire bonding techniques, or connecting external electrical circuits to the cell via three dimensional interconnections.

In embodiments, the top substrate 502 may be an optional element. In embodiments, each pair of metal conductors 516 may include a top metal plate that is placed in proximity to a bottom metal plate to thereby form a capacitor. During operation, the deflection of the membrane 504 due to an external pressure wave may be measured by measuring the variation of the capacitance of the metal conductors 516. In embodiments, a light source, such as laser, 514 may be placed in proximity to the membrane 504 so that the light emitted by the light source 514 may pass through the aperture/perforation 512 in the membrane 504. In embodiments, the light from the aperture 512 may be used to align the top substrate 502 with respect to the bottom substrate 501 when the top substrate is bonded to the bottom substrate.

In embodiments, the top substrate 502 may be an ASIC chip, where the ASIC chip includes electrical, electronic, or photonic elements for controlling the piezoelectric elements 520a-520c. The top substrate 502 may be connected to the electrical connections in the membrane 504 through a number of techniques including, but not limited to, electrical through vias, flip-chip bonding, eutectic bonding or other lead transfer techniques commonly used in micro-machined devices. In embodiments, the ASIC chip may include multiple bumps, and the bumps may be connected to electrical circuits on the membrane 504 by vertical interconnections or by wire bonding.

Figure 6:
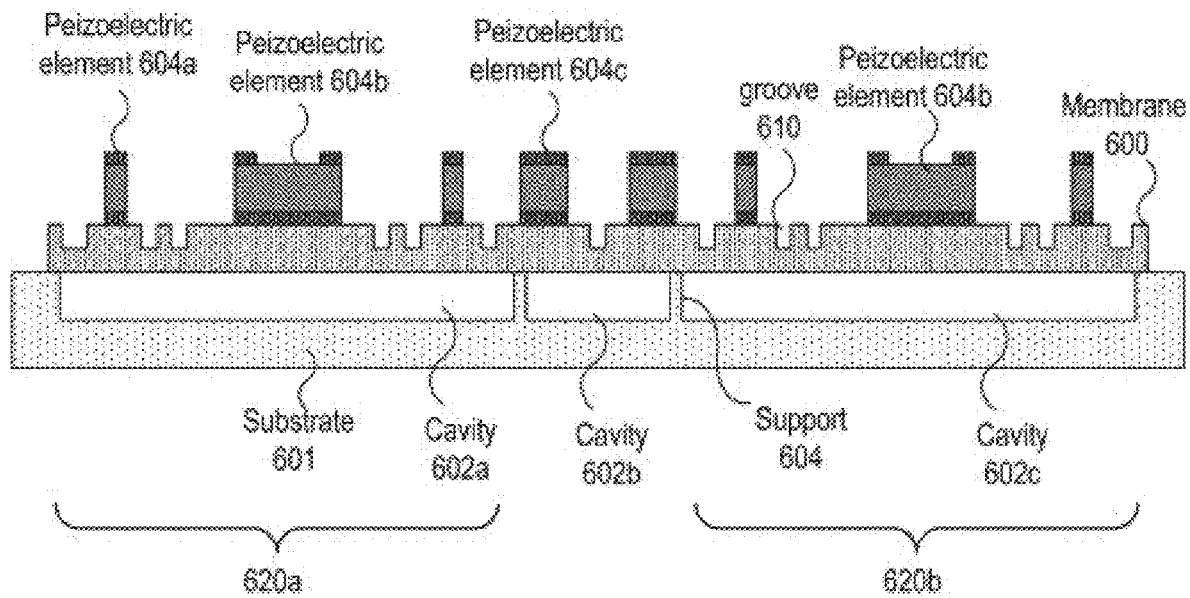
FIGS. 6-7 show schematic cross-sectional views of transceiver cells according to embodiments of the present disclosure.
Figure 7:
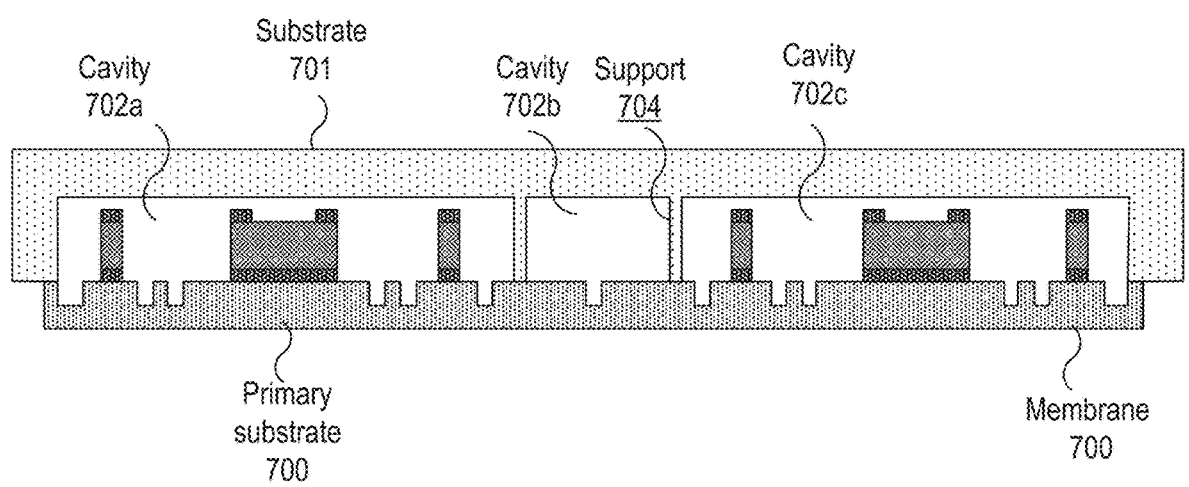

FIGS. 6-7 show schematic cross sectional views of transceiver cells according to embodiments of the present disclosure. As depicted in FIG. 6, the membrane 600 may suspend from a substrate 601 at both ends and maintain a spaced-apart relationship with the substrate 601 by one or more mechanical supports 604. In embodiments, one or more piezoelectric elements 604a-604c may be disposed on the top surface of the membrane. It is noted that one or more piezoelectric elements may be disposed on the bottom surface of the membrane 600, as in FIG. 5. Also, one or more grooves 610 or bumps may be formed on the top surface (and/or bottom surface) of the membrane so that the thickness of the membrane is varied.

In embodiments, one or more cavities 602a-602c may be formed between the membrane 600 and the substrate 601, and the gas pressures inside the cavities may be adjusted so that the vibrational motion of the corresponding portions of the membrane may be controlled. For instance, the cavity 602a may be in vacuum so that the portion 620a of the membrane can freely move in the vertical direction, while the cavity 602c may be filled with gas so that the vibrational motion of the portion 620c of the membrane may be damped by the gas.

In embodiments, the membrane 600 may be bonded to a substrate 601 using commonly used substrate bonding and attachment techniques, such as but not limited to, anodic bonding, silicon fusion bonding, eutectic bonding, glass-frit bonding, solder attach etc., to create a vacuum (e.g., 602a) or an air gaps (e.g., 602b and 602c) under the membrane 600. The bonding may allow rapid attenuation of acoustic energy in the vacuum or air gap and protect the membrane from moisture or other reactants.

Figure 6A:
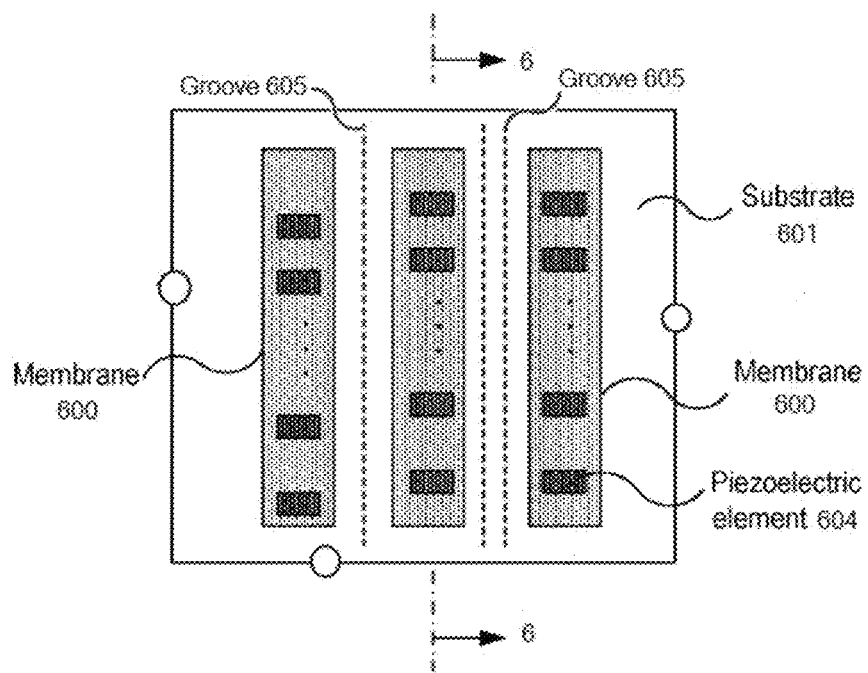
FIG. 6A shows a top view of the transceiver cell of FIG. 6 according to embodiments of the present disclosure.

In embodiments, various types of active or passive elements may be incorporated in between transceiver cells to reduce the acoustic cross talk between the cells. For instance, the substrate 601 may include grooves 605 (shown in FIG. 6A) to attenuate the cross talk. In another example, the bonding of the membrane 600 to the substrate 601 may reduce the cross talk. In addition to these passive cross talk attenuation mechanisms, one or more of the piezoelectric elements 604a-604c may be actuated to actively attenuate the cross talk. Such active crosstalk attenuation features may be electrically excited to physically dampen mechanical vibration of the supports of the membrane.

In FIG. 7, the membrane 700 may suspend from a substrate 701 at both ends and maintain a spaced-apart relationship with the substrate 701 by one or more supports 704. Also, one or more cavities 702a-702c may be formed between the substrate 701 and the membrane 704, where the cavities 702 may have similar functions as the cavities 602a-602c. In embodiments, the membrane 700 may be bonded to a substrate 701 using commonly used substrate bonding and attachment techniques, such as but not limited to, anodic bonding, silicon fusion bonding, eutectic bonding, glass-frit bonding, solder attach etc. In embodiments, the substrate 701 may be an ASIC chip that includes electrical, electronic, or photonic elements for controlling the piezoelectric elements attached to the membrane 700, and the substrate 701 may be electrically connected to the membrane 700 by vertical interconnections or by wire bonding.

Figure 8:
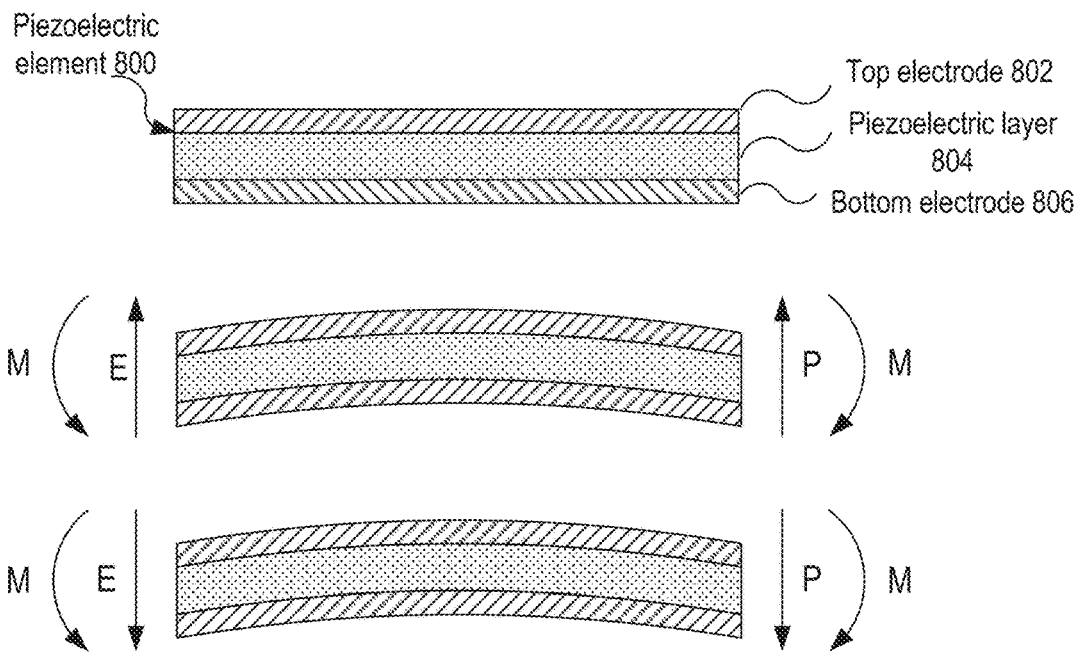
FIG. 8 illustrates a mechanism to generate a bending moment in a piezoelectric element according to embodiments of the present disclosure.

FIG. 8 illustrates a mechanism to generate a bending moment in a piezoelectric element 800 according to embodiments of the present disclosure. As depicted, the piezoelectric element 800 may include a top electrode 802, a piezoelectric layer 804 and a bottom electrode 806, where the piezoelectric layer 804 may be polarized (indicated by arrows P) in either upward or downward direction. In embodiments, the electrical field (indicated by arrows E) may be generated when an electrical potential is applied across the top electrode 802 and the bottom electrode 806. Depending on the polarization direction, the piezoelectric element 800 may generate different bending moments (indicated by arrows M). In the Tx mode/process, the bending moment generated by the piezoelectric element 800 may be transferred to the underlying membrane and cause the membrane to vibrate, generating pressure waves.

In embodiments, the polarization P of the piezoelectric layer 804 may be changed by a process called poling. In embodiments, the poling process may include application of a high voltage across the top and bottom electrodes at a temperature above the Curie point for a predetermine time period. In embodiments, depending on the thickness and material of the piezoelectric layer 804, the voltage for the poling process may be changed. For instance, for a 1 μm thick piezoelectric layer, the voltage potential may be about 15V.

In embodiments, a piezoelectric element may have more than two electrodes. For instance, the piezoelectric element 502c may have two top electrode and one bottom electrode. In embodiments, a first portion of the piezoelectric layer below the first top electrode may be poled in a first direction and a second portion of the piezoelectric layer below the second electrode may be poled in a second direction, where the first direction may be parallel or opposite to the second direction.

Figure 9:
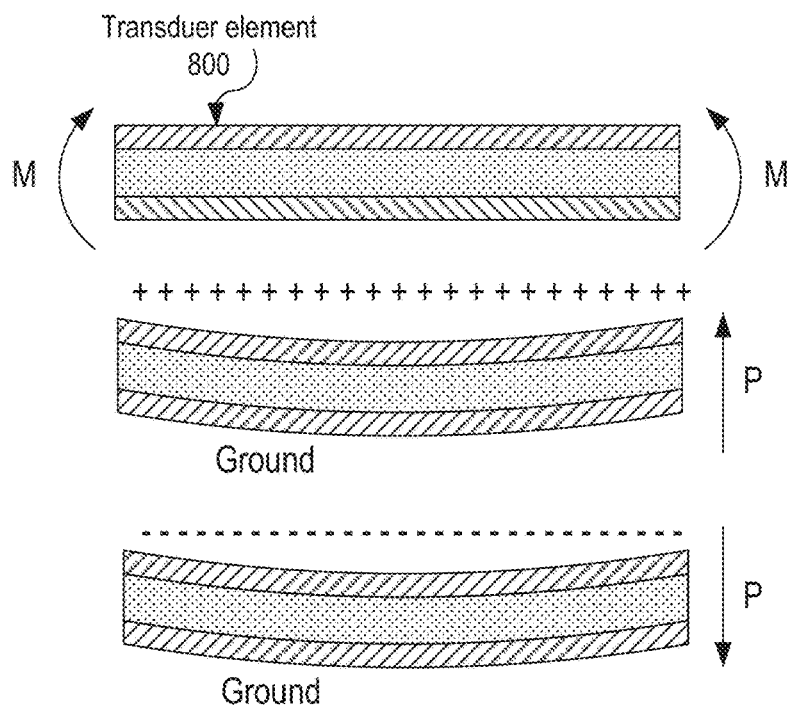
FIG. 9 illustrates a mechanism to develop an electrical charge on a piezoelectric element according to embodiments of the present disclosure.

FIG. 9 illustrates a mechanism to develop an electrical charge on the piezoelectric element 800 according to embodiments of the present disclosure. As depicted, the piezoelectric element 800 may generate an electrical charge upon applying a bending moment M. In embodiments, the piezoelectric element 804 may be polarized in either upward or downward direction. Depending on the polarization direction, the electrical charge developed on each piezoelectric element 800 may have a different polarity. In embodiments, the bottom electrode 806 may be connected to the ground or a predetermined voltage bias.

In the Rx mode/process, the membrane may be bent by the external pressure waves, such as the pressure wave reflected from the internal organ 112, and the bending of the membrane may be transferred to the piezoelectric element 800, developing an electrical charge on the piezoelectric element. Using this electrical charge, the intensity of the pressure waves may be measured. Also, the electrical charges developed by multiple piezoelectric elements may be processed to get the image of the internal organ 112.

In embodiments, there may be a further benefit in varying the thickness of a membrane, referred to as corrugating the membrane, to create regions where selective application of bending moments may further change the deflection profile of the membrane. This is referred to as "stress shaping." In embodiments, the combination of stress shaping and selective arrangement or attachment of piezoelectric elements to different parts of the membrane may be used to deflect the membrane in a predetermined manner.

Figure 10:
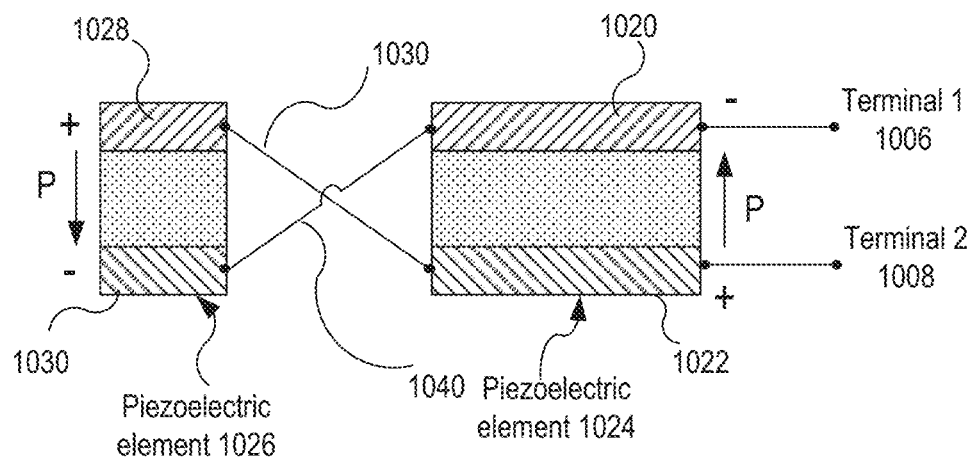
FIGS. 10-11 show schematic diagrams of electrical connections to multiple piezoelectric elements according to embodiments of the present disclosure.
Figure 11:
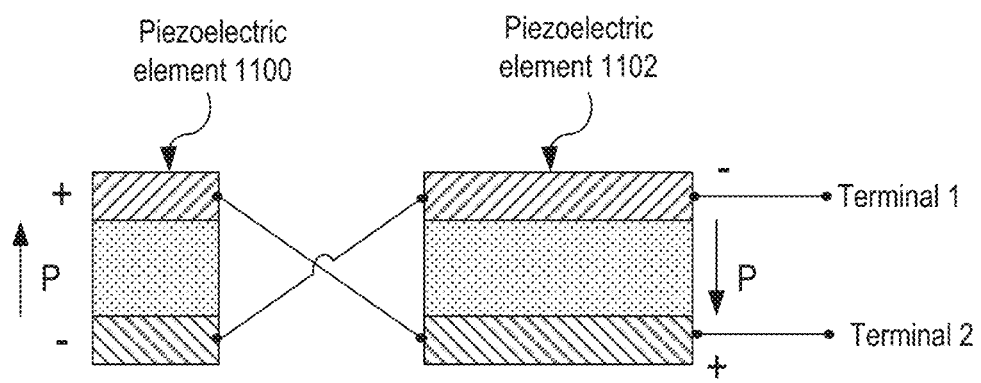

FIGS. 10-11 show schematic diagrams of electrical connections to multiple piezoelectric elements according to embodiments of the present disclosure. For the purpose of illustration, the piezoelectric elements 1024 and 1026 are assumed to be two-terminal devices, i.e., each piezoelectric element has two electrodes, even though each piezoelectric element may have more than two electrodes. Also, the piezoelectric elements 1024 and 1026 may be electrically coupled to two electrical ports/terminals 1006 and 1008.

In FIG. 10, a top electrode 1020 of a first piezoelectric element 1024 may be connected to a bottom electrode 1030 of a piezoelectric element 1026 by means of an electrical connection 1030, and the top electrode 1020 may be coupled to an electrical terminal 1006. Similarly, a bottom electrode 1022 of the first piezoelectric element 1024 may be connected to a top electrode 1028 of a second piezoelectric element 1026 by means of the electrical connection 1040 and the bottom electrode 1022 may be coupled to an electrical terminal 1008. In embodiments, this configuration of the electrical connection may allow different piezoelectric elements to be polarized in opposite directions by using two electrical terminals. In embodiments, the same two terminals 1006 and 1008 may also be used in the Tx and Rx modes. This technique can be easily expanded to multiple piezoelectric elements within a membrane or a cell to be operated via two terminals 1006 and 1008.

In FIG. 11, the polarization of each of the piezoelectric elements 1102 and 1104 may be opposite to the polarization of the corresponding piezoelectric element in FIG. 10. As such, in the Tx mode/process, the piezoelectric elements 1102 and 1104 may generate a bending moment that is opposite to the bending moment generated by the piezoelectric elements 1024 and 1026. Likewise, in the Rx mode/process, the piezoelectric elements 1102 and 1104 may develop an electrical charge that is opposite to the electrical charge developed by the piezoelectric elements 1024 and 1026.

In embodiments, one advantage of the electrical configurations in FIGS. 10 and 11 is that each of the piezoelectric elements may be operated as a "two-port" electrical device. In a two-port configuration, only two electrical ports/terminals 1006 and 1008 may be needed even if multiple separate piezoelectric elements may be disposed on the membrane. In embodiments, the two-port electrical configuration may significantly reduce the number of interconnects required to operate devices and be advantageous in creating large tiles in addition to simplification of transmit and receive mode electronics.

Figure 12:
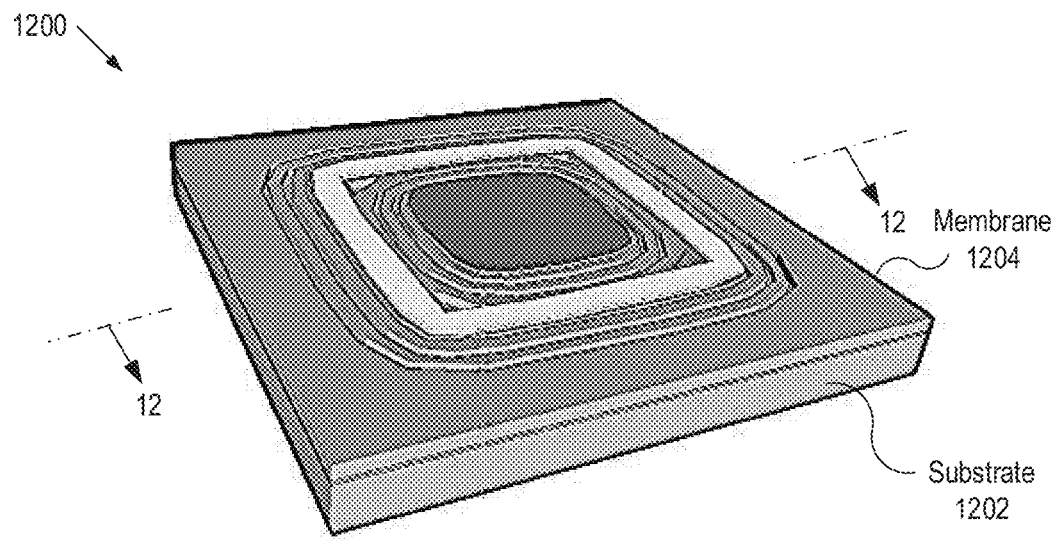
FIG. 12 shows a perspective view of an exemplary membrane coupled with multiple piezoelectric elements according to embodiments of the present disclosure.
Figure 13:
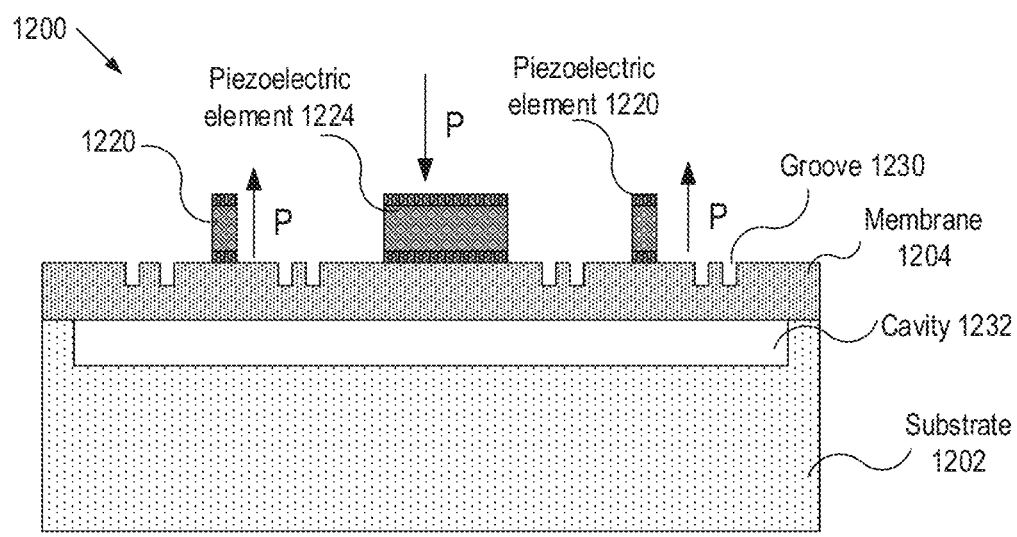
FIG. 13 shows a cross sectional view of the membrane in FIG. 12 according to embodiments of the present disclosure.

In embodiments, multiple membranes may be used in a single cell to increase the acoustic output from the cell. Alternately, some of the membranes in a cell may be designed to operate at a different resonant frequency. FIG. 12 shows a perspective view of a transducer element 1200 according to embodiments of the present disclosure. FIG. 13 shows a cross sectional view of the transducer element in FIG. 12, taken along the line 12-12, according to embodiments of the present disclosure. As depicted, the transducer element 1200 may include a membrane 1204 coupled with multiple piezoelectric elements 1220 and 1224. When viewed from the top, the inner piezoelectric element 1224 may have a rectangular shape with rounded corners while the outer piezoelectric element 1220 may have a shape of belt and surround the piezoelectric element 1224. In embodiments, the inner piezoelectric element 1224 may be polarized downwardly, while the outer piezoelectric element 1220 may be polarized upwardly. The membrane 1204 may have one or more grooves 1230 so that the thickness of the membrane is 1204 changed. The membrane 1204 may suspend from the substrate 1202 and the substrate 1202 may have a cavity 1232 so that the membrane 1204 may vibrate without touching the top surface of the substrate 1202. In embodiments, the cavity 1232 may be in vacuum or filled with a gas at a predetermined pressure.

Figure 14:
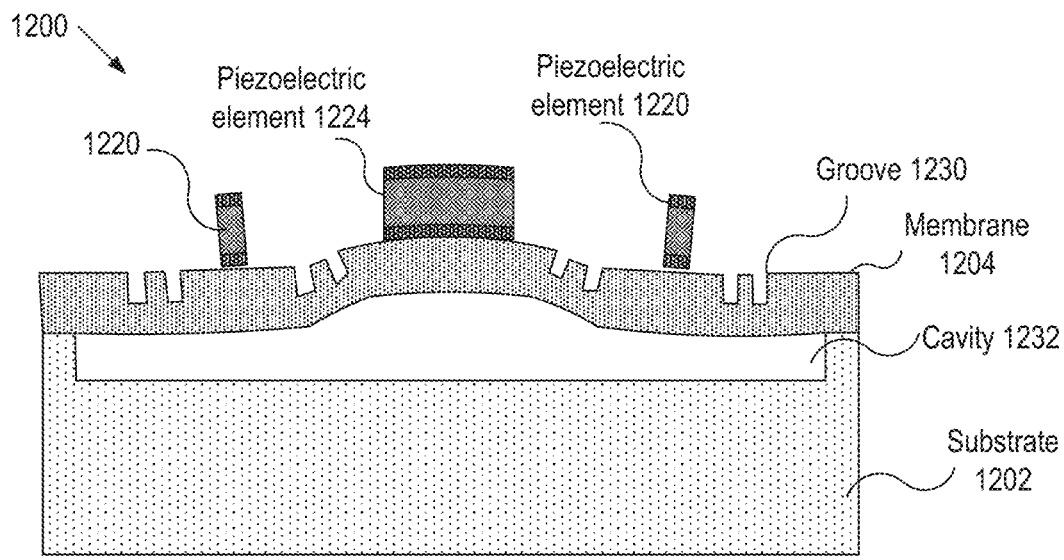
FIG. 14 shows a numerical simulation of the membrane in FIG. 13 in a transmission mode/process according to embodiments of the present disclosure.

In embodiments, in the Tx mode/process, application of appropriate electrical signals across the piezoelectric elements 1220 and 1224 may generate a piston motion of the membrane 1204. FIG. 14 shows a numerical simulation of the membrane 1204 in the Tx mode/process according to embodiments of the present disclosure. As depicted, the central portion of the membrane 1204 may have a piston motion (i.e., move upwardly) when electrical fields are applied to the piezoelectric elements 1220 and 1224 on the corrugated membrane 1204. In embodiments, the piston motion may lead to a significant increase in the acoustic output since the pressure level is directly proportional to the volumetric displacement of the membrane 1204. Simulation results indicate that the piston motion may increase the acoustic transmission by 9 dB, compared to a simple bending motion of the membrane.

Figure 15:
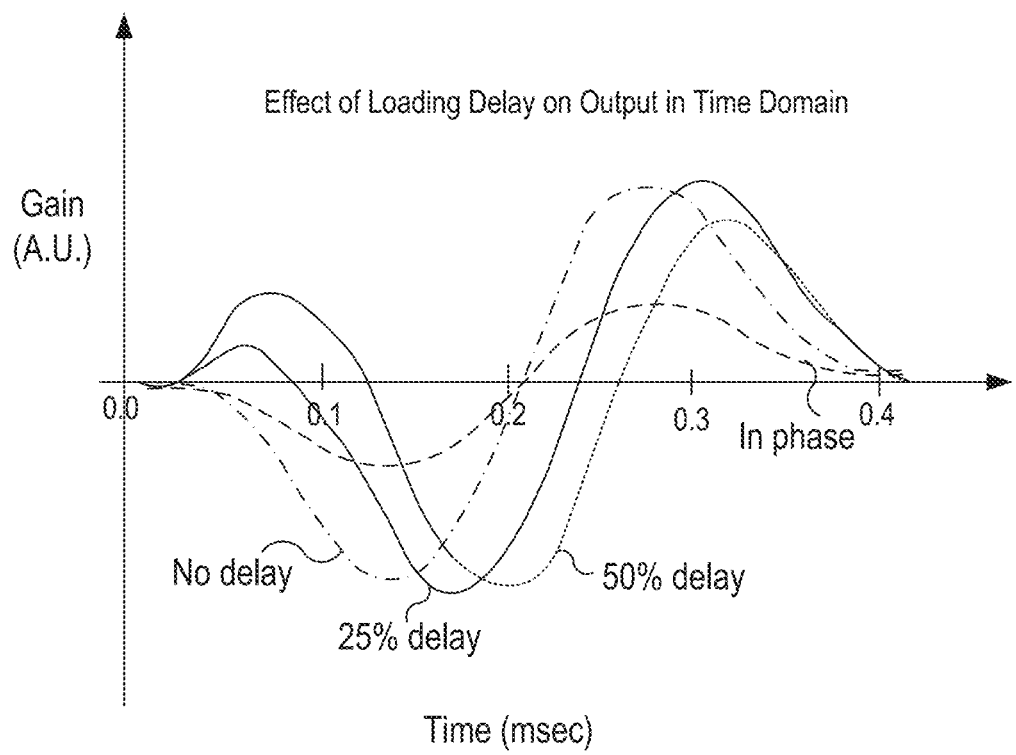
FIG. 15 shows a plot of gains of the membrane in FIG. 12 as a function of time delay according to embodiments of the present disclosure.

In embodiments, by adjusting a time delay or a phase delay between the electrical signals that activate the piezoelectric elements 1220 and 1224, an increase in the displacement (gain) of the central portion of the membrane may be achieved. FIG. 15 shows a plot of gains of the membrane 1204 as a function of time/phase delay according to embodiments of the present disclosure. As depicted, the displacement (gain) of the central portion of the membrane 1204 may reach its maximum value when the phase delay between the electrical signals for driving the piezoelectric elements 1220 and 1224 is about 90 degrees.

In embodiments, in the Rx mode/process, opposite bending moments may be developed in different portions of the membrane 1204. Since the piezoelectric elements 1220 and 1224 are polarized in opposite directions, a charge of the same polarity may be developed on both piezoelectric elements. In embodiments, the electrical connections to the piezoelectric elements 1220 and 1224 may be arranged to collect the charges of the same polarity. According to simulation results, the use of two oppositely polarized elements may increase the charge development by about 50%, compared to the case where only one polarization is used.

Figure 16:
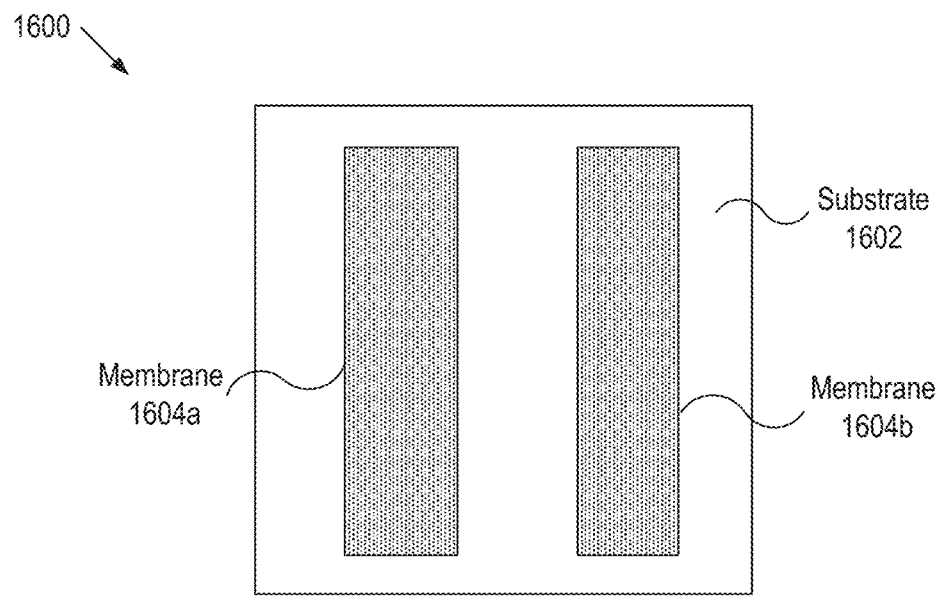
FIG. 16 shows a schematic diagram of a transceiver cell having multiple membranes that have different resonance frequency characteristics according to embodiments of the present disclosure.

FIG. 16 shows a schematic diagram of a transceiver cell 1600 having multiple membranes 1604a and 1604b that have different resonance frequency characteristics according to embodiments of the present disclosure. As depicted, the multiple membranes 1604a and 1604b may be disposed on a substrate 1602. In embodiments, the dimension of the membranes and the separation of the membranes may be maintained at a fraction of the principal wavelength of the emitted sound, which may increase the bandwidth of the transducer cell 1600.

Figure 17:
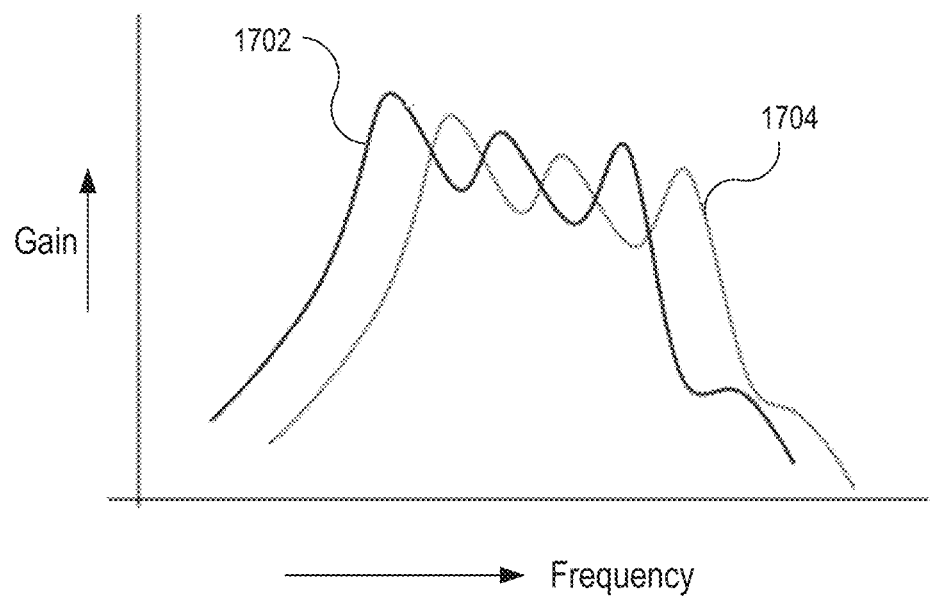
FIG. 17 shows a plot of gains of the membranes in FIG. 16 as a function of frequency according to embodiments of the present disclosure.

FIG. 17 shows a plot of gains of the membranes 1604a and 1604b as a function of frequency according to embodiments of the present disclosure. In embodiments, the membranes 1604a and 1604b may have different resonance frequency characteristics 1702 and 1704, respectively.

In embodiments, a transducer cell with increased bandwidth may be desirable as it may be operated in a harmonic imaging mode, i.e., a Tx mode frequency is different from an Rx mode frequency. In an embodiment that uses the harmonic imaging, a first pulse is sent to drive the piezoelectric elements followed by a second pulse, where the piezoelectric elements are driven by the second pulse in an anti-phase to the first pulse. This technique is commonly referred to as pulse-inversion.

In embodiments, multiple membranes in a transceiver cell may be designed to transmit or receive at different frequencies by changing one or more of the following design points: (1) the corrugation pattern of the membrane, (2) shape of the piezoelectric elements, (3) physical dimensions of the membrane, and (4) polarization of the piezoelectric elements.

Figure 18A:
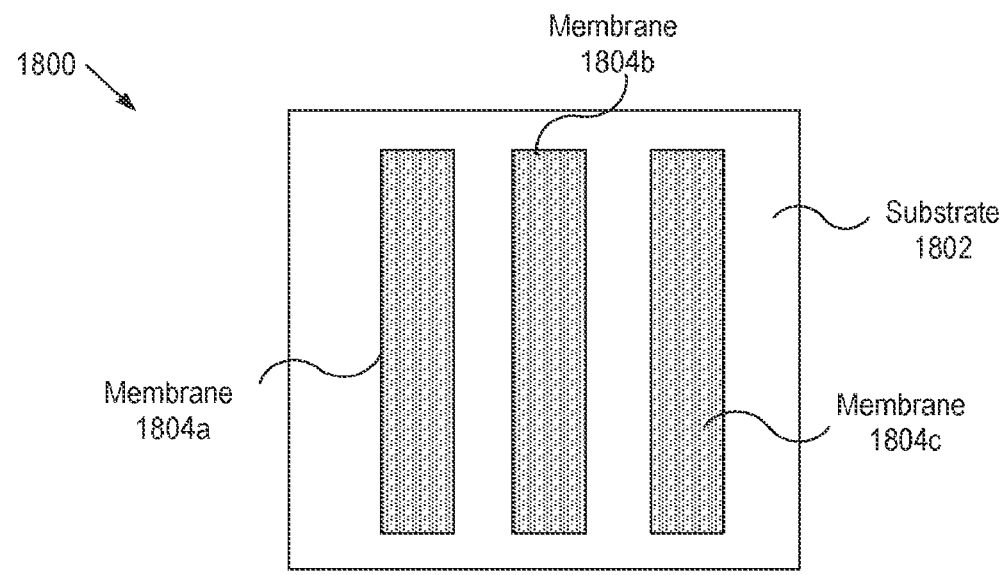
FIG. 18A shows a schematic diagram of a transceiver cell having multiple membranes that have different resonance frequency characteristics according to embodiments of the present disclosure.
Figure 18B:
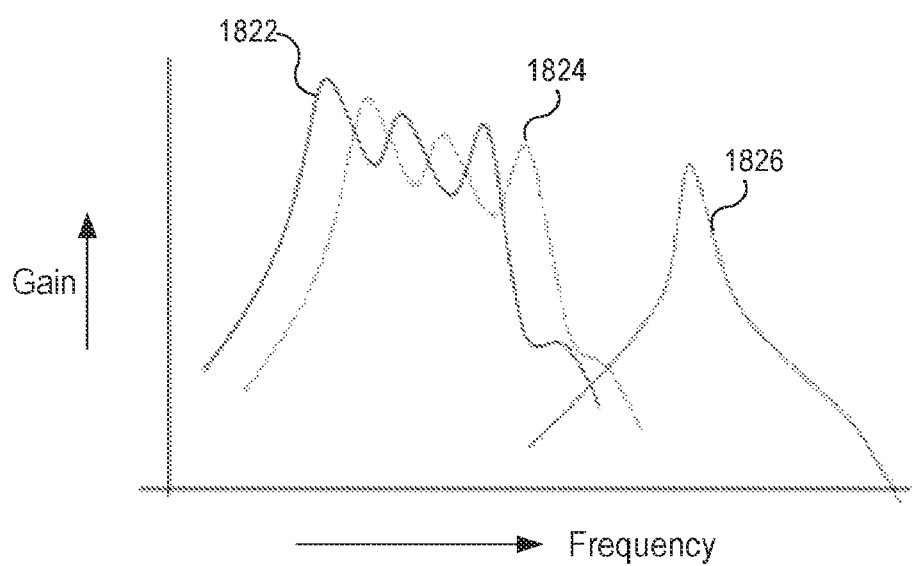
FIG. 18B shows a plot of gains of the membranes in FIG. 18A as a function of frequency according to embodiments of the present disclosure.

FIG. 18A shows a schematic diagram of a transceiver cell 1800 including a substrate 1802 and multiple membranes 1804a-1804c that have different resonance frequency characteristics according to embodiments of the present disclosure. FIG. 18B shows a plot of gains of the membranes 1804a-1804c as a function of frequency according to embodiments of the present disclosure. In FIG. 18B, the curves 1822, 1824 and 1826 correspond to the membranes 1804a, 1804c and 1804b, respectively. As depicted, the frequency corresponding to the peak gain of the membrane 1804b may be separated from the frequencies corresponding to the peak gains of the membranes 1804a and 1804c.

In embodiments, the membranes 1804a and 1804c may be operated in both Tx and Rx mode while a membrane 1804b may be operated in the Rx mode only. The resonance frequencies of the membranes 1804a and 1804c may be designed to increase the bandwidth of the transducer by tuning the frequency-gain responses of the membranes 1804a and 1804c, while the membrane 1804b may be designed to operate in the Rx mode only and receive a harmonic response of the Tx mode.

Figure 19A:
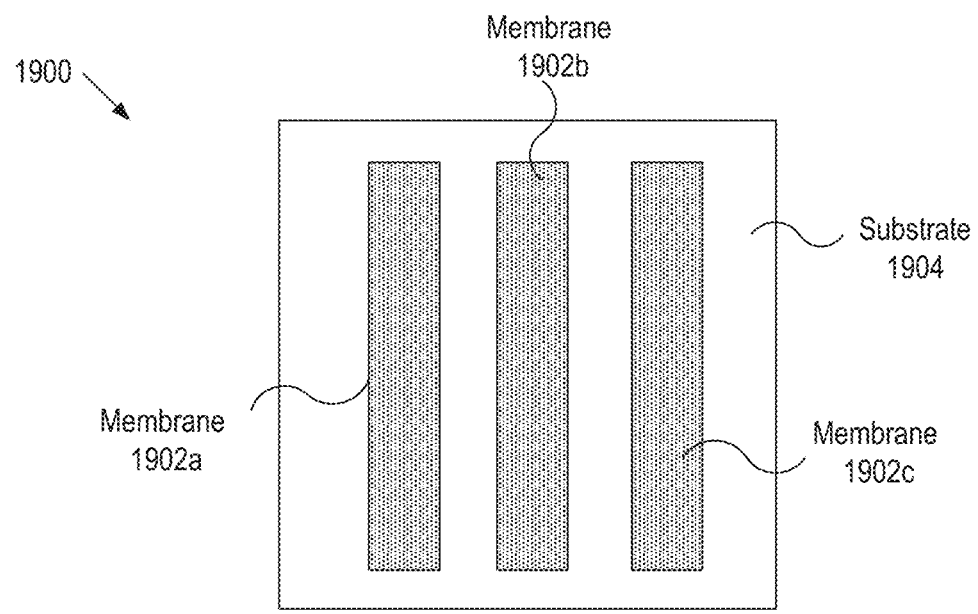
FIG. 19A shows a schematic diagram of a transceiver cell having multiple membranes that have different frequency responses according to embodiments of the present disclosure.
Figure 19B:
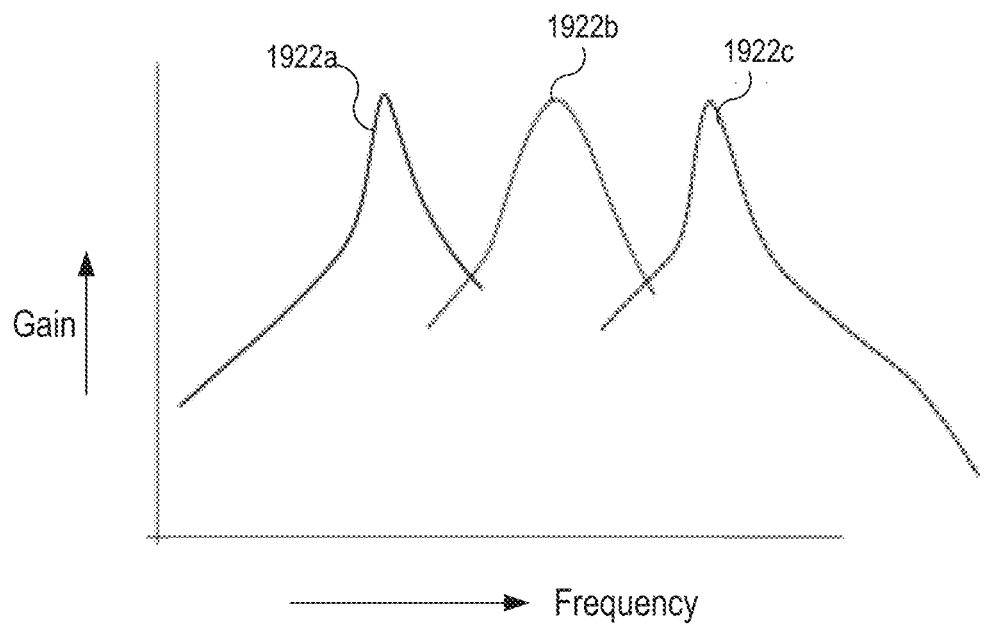
FIG. 19B shows a plot of gains of the membranes in FIG. 19A as a function of frequency according to embodiments of the present disclosure.

FIG. 19A shows a schematic diagram of a transceiver cell 1900 having multiple membranes 1902a-1902c that have different frequency responses according to embodiments of the present disclosure. As depicted, the three membranes 1902a-1902c may be disposed on a substrate 1904. FIG. 19B shows a plot of gains of the membranes in FIG. 19A as a function of frequency according to embodiments of the present disclosure. In FIG. 19B, the curves 1922a-1922c may correspond to the membranes 1902a-1902c, respectively. As depicted, the three membranes 1902a-1902c may have different frequency responses and the frequencies at the maximum gains are separated from each other, increasing the bandwidth of the transducer cell. As the transducer cell 1900 may have an increased bandwidth, the transducer cell may be operated in a harmonic imaging mode, i.e., a Tx mode frequency is different from an Rx mode frequency.

Figure 20:
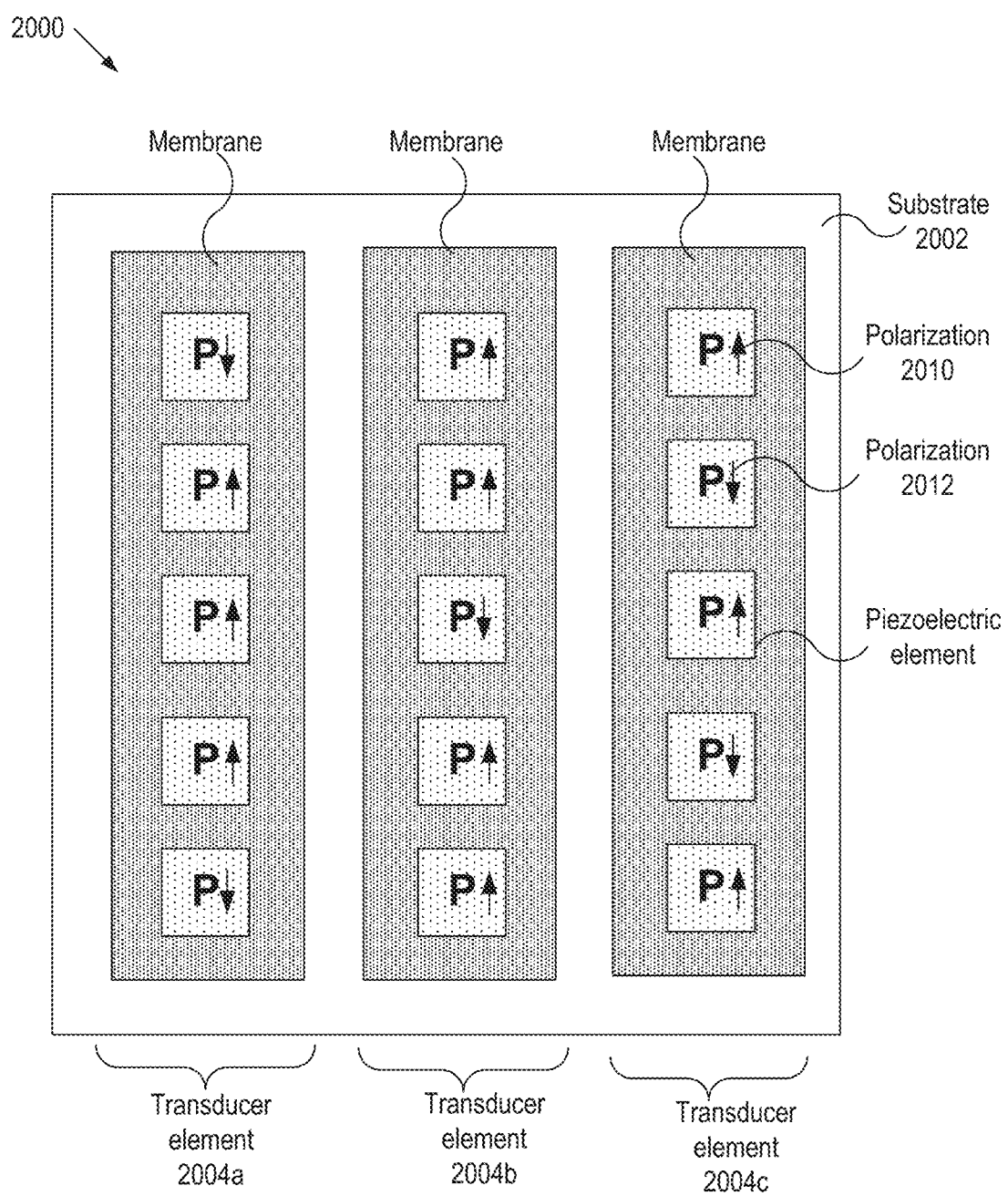
FIG. 20 shows a schematic diagram of a transceiver cell having multiple membranes according to embodiments of the present disclosure.

FIG. 20 shows a schematic diagram of a transceiver cell 2000 having multiple transducer elements 2004a-2004c according to embodiments of the present disclosure. As depicted, the transducer elements 2004a-2004c may be disposed on a substrate 2002, and each transducer element may include a membrane, preferably a corrugated membrane, and multiple piezoelectric elements disposed on the membranes. As depicted, the polarization direction of each piezoelectric element on the membranes is indicated by an upward arrow 2010 or a downward arrow 2012.

Figure 21A:
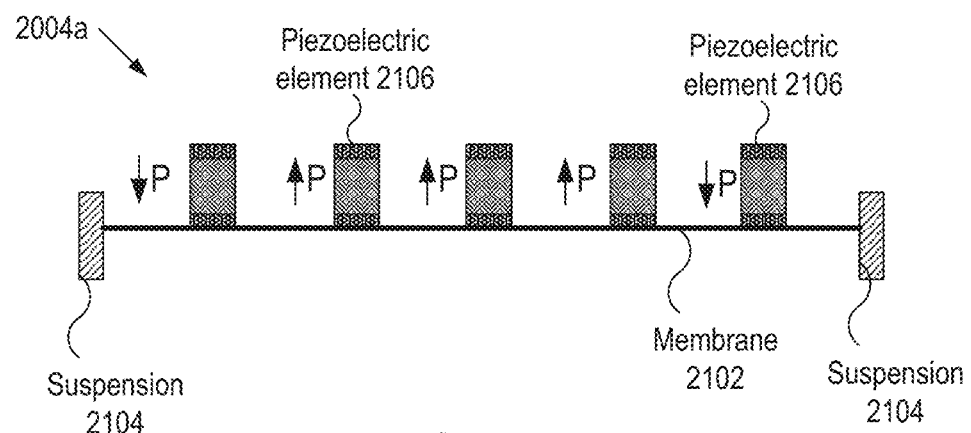
FIG. 21A shows a cross sectional view of one of the membranes in FIG. 20 according to embodiments of the present disclosure.

FIG. 21A shows a membrane actuated in a first mode of resonance according to embodiments of the present disclosure. As depicted, the transducer element 2004a may include a membrane 2102 that may suspend from the substrate 2002 by a suspension mechanism 2104. Multiple piezoelectric elements 2106 may be disposed on the membrane 2102, where each piezoelectric element may be polarized either upwardly or downwardly, as indicated by the arrows P.

Figure 21B:
FIG. 21B shows the membrane in FIG. 21A actuated in a first mode of resonance according to embodiments of the present disclosure.

When a suitable electrical signal is applied to the piezoelectric elements 2106 on the membrane 2102, the membrane 2102 may vibrate in the first resonance mode. FIG. 21B shows the membrane 2102 actuated in a first mode of resonance according to embodiments of the present disclosure. (For simplicity, the piezoelectric elements 2016 are not shown in FIG. 21B.)

Figure 22A:
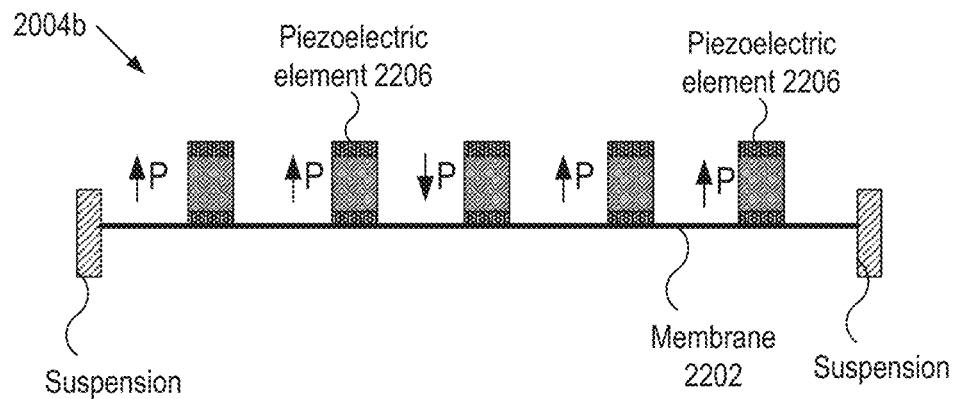
FIG. 22A shows a cross sectional view of one of the membranes in FIG. 20 according to embodiments of the present disclosure.
Figure 22B:
FIG. 22B shows the membrane in FIG. 22A actuated in a third mode of resonance according to embodiments of the present disclosure.

In embodiments, the polarities of the piezoelectric elements on a membrane may be arranged so that the membrane may vibrate in a different resonance mode. FIG. 22A shows a cross sectional view of the transducer element 2004b according to embodiments of the present disclosure. FIG. 22B shows the membrane 2202 actuated in a third mode of resonance according to embodiments of the present disclosure. The transducer element 2004b may be similar to the transducer element 2002b, with the difference that the piezoelectric elements 2206 have different polarities from the piezoelectric elements 2106. As depicted in FIG. 22B, the membrane 2202 may vibrate in the third mode of resonance when an electric field is applied to the piezoelectric elements 2206.

Figure 23A:
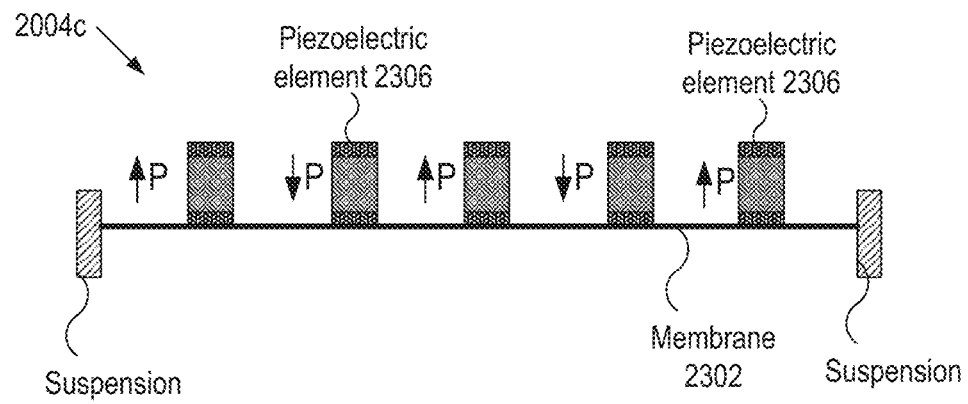
FIG. 23A shows a cross sectional view of one of the membranes in FIG. 20 according to embodiments of the present disclosure.
Figure 23B:
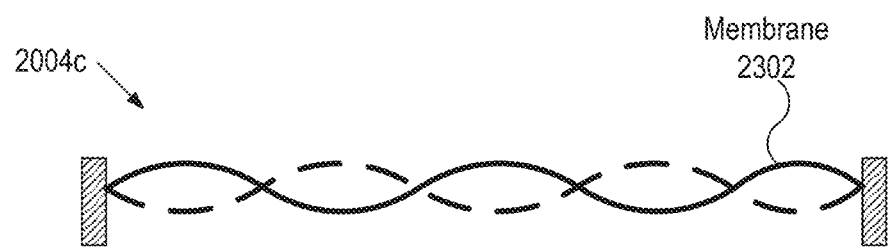
FIG. 23B shows the membrane in FIG. 23A actuated in a fifth mode of resonance according to embodiments of the present disclosure.

FIG. 23A shows a cross sectional view of a transducer element 2004c according to embodiments of the present disclosure. FIG. 23B shows a membrane 2302 actuated in a fifth mode of resonance according to embodiments of the present disclosure. As depicted, the transducer element 2004c may be similar to the transducer element 2004a, with the difference that the piezoelectric elements 2306 have different polarities from the piezoelectric elements 2106. As depicted in FIG. 23B, the membrane 2302 may vibrate in the fifth mode of resonance when an electric field is applied to the piezoelectric elements 2306.

In embodiments, in the Rx mode/process, applications of external pressure waves of different frequencies may lead to excitations of the membranes at different modes. In embodiments, the polarization of the piezoelectric elements may be arranged so that the external pressure waves may create electrical charges having the same polarity across each membrane. One of the benefits of such a configuration is that it may allow unprecedented control over shaping the frequency responses of membranes in the Tx and Rx modes.

Figure 24A:
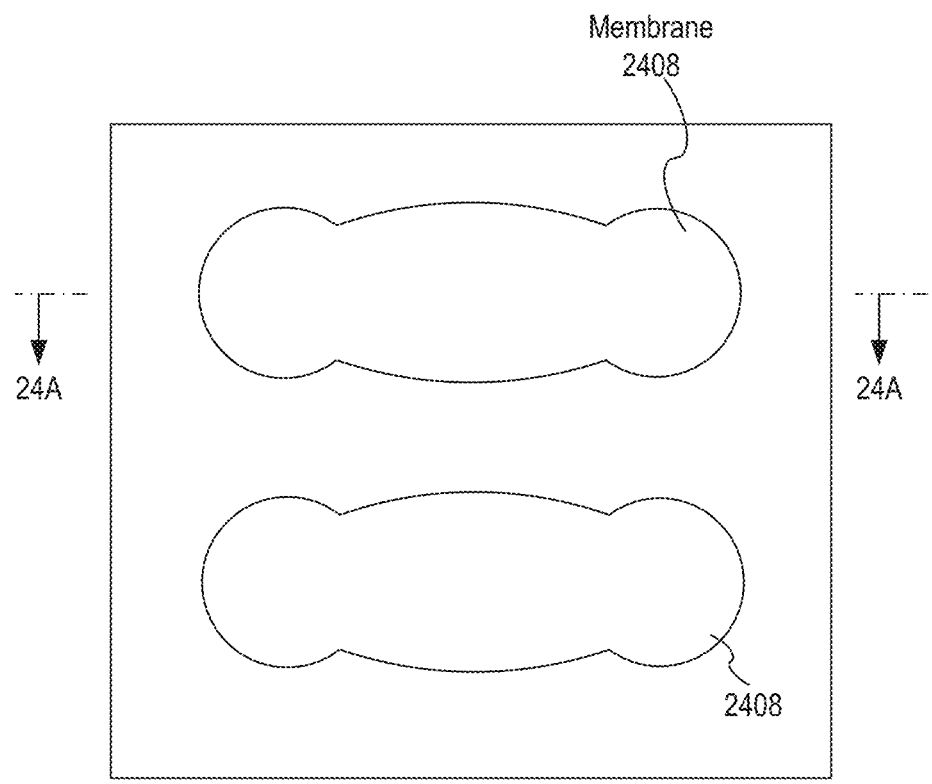
FIG. 24A-28 show steps for fabricating an exemplary transceiver cell that has two membranes according to embodiments of the present disclosure.
Figure 24B:
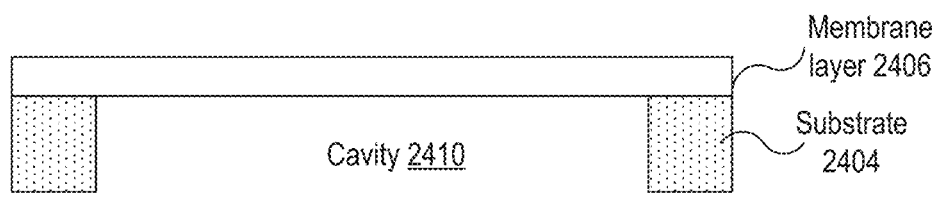

FIG. 24A-28 show steps for fabricating an exemplary transceiver cell that has two membranes according to embodiments of the present disclosure. FIG. 24A shows a top view of the two membranes 2408 disposed on a substrate 2404 and FIG. 24B shows a cross sectional view of the membrane and substrate, taken along the line 24-24 according to embodiments of the present disclosure. As depicted, in embodiments, the membranes 2408 may be formed by depositing a membrane layer 2406 on the substrate 2404 and two cavities 2410 may be formed to remove portions of the substrate 2404, to thereby form the membranes 2408 that may vibrate relative to the substrate 2404 in a vertical direction. In embodiment, the cavities 2410 may be formed by conventional wafer processing techniques, such as etching. In embodiments, the substrate 2404 may be formed of the same material as the membrane layer 2406. In alternative embodiments, the substrate 2404 may be formed of a different material from the membrane layer 2406. It is noted that the cavities 2410 may be formed after the other components, such as top conductor (2802 in FIG. 28), of the transducer cell is formed.

Figure 25:
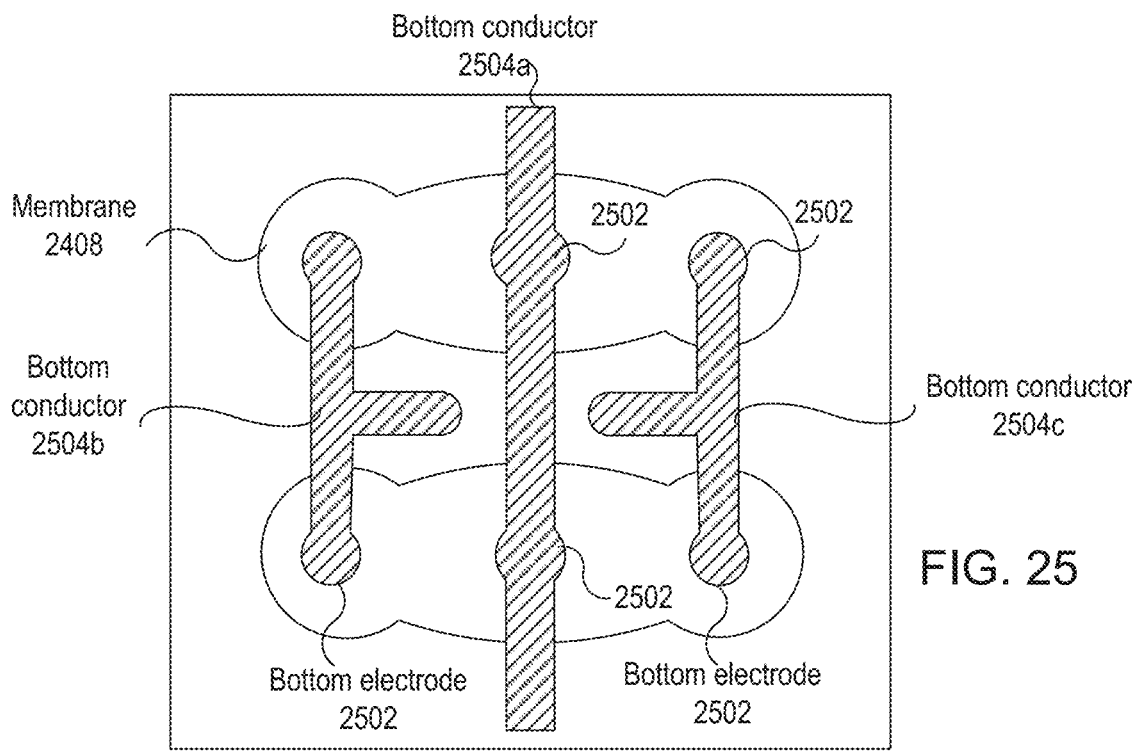

FIG. 25 shows bottom electrodes 2502 and three bottom conductors 2504a-2504c according to embodiments of the present disclosure. As depicted, each of the membranes 2408 may have three bottom electrodes 2502 and each of the bottom electrodes 2502 may be electrically connected to one of the three bottom conductors 2504a-2504c. In embodiments, the bottom electrodes 2502 may be formed of a first metal and the bottom conductors 2504a-2504c may be formed of a second metal, where the first metal may be the same as (or different from) the second metal.

Figure 26:
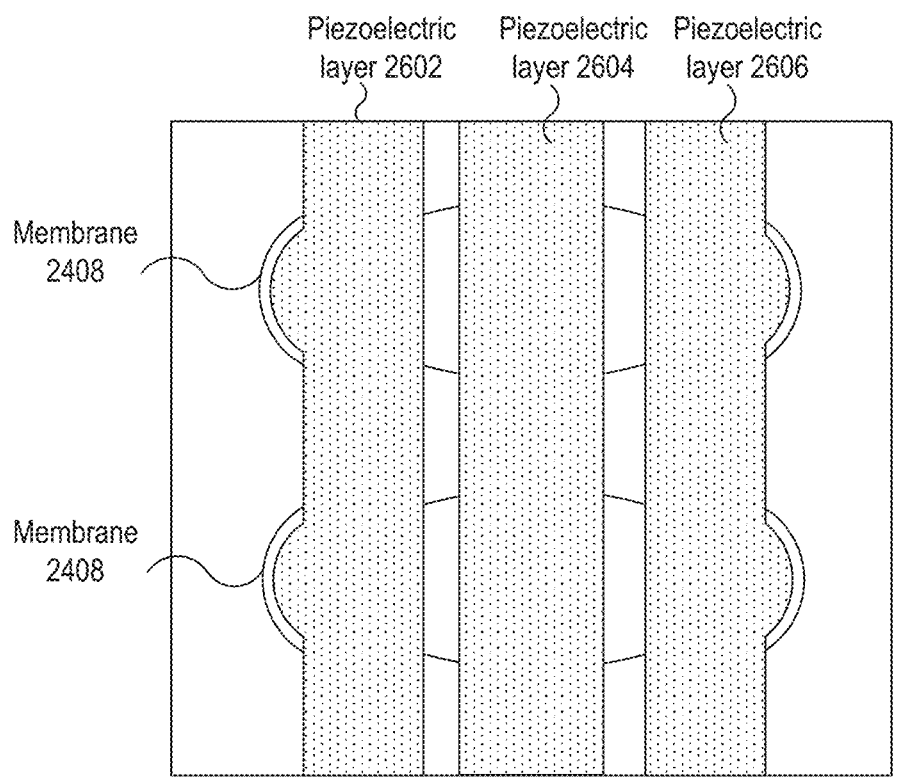
Figure 27:
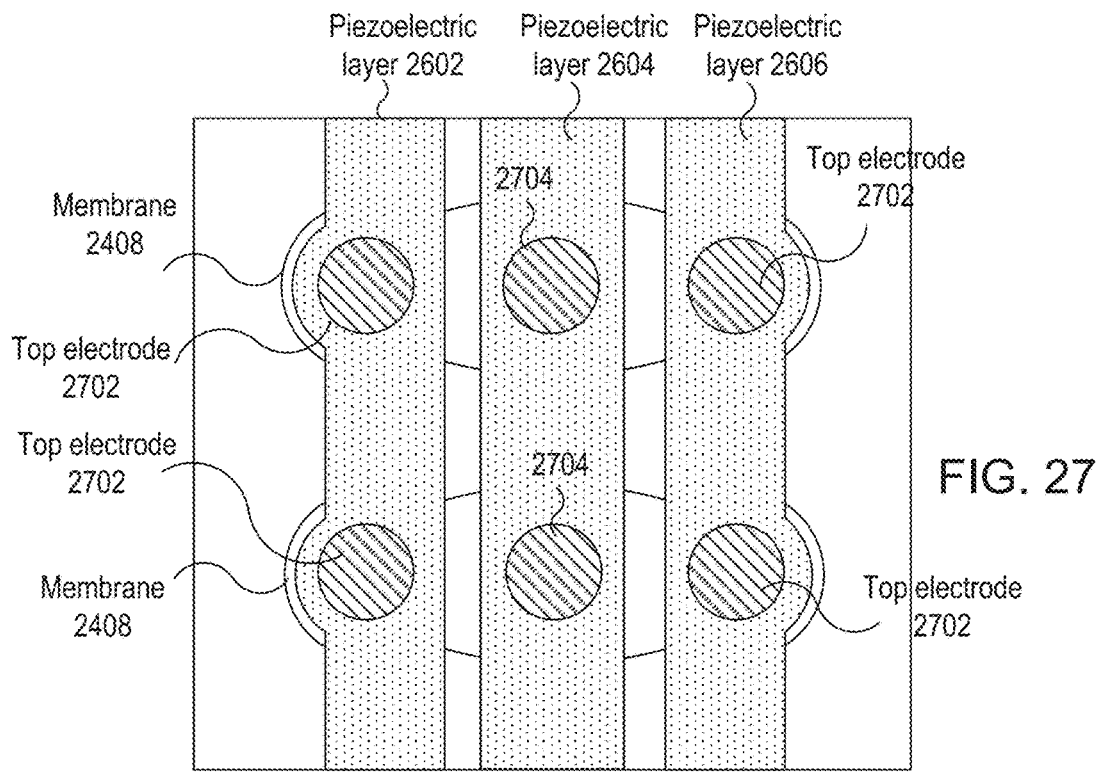

FIG. 26 shows piezoelectric layers 2602, 2604 and 2606 disposed over the six bottom electrodes 2502 and three bottom conductors 2504a-2504c according to embodiments of the present disclosure. FIG. 27 shows top electrodes 2702 and 2704 disposed on the piezoelectric layers 2602, 2604 and 2606 according to embodiments of the present disclosure. As depicted, three top electrodes may be formed over each membrane 2408, i.e., each membrane 2408 may include three piezoelectric elements. In embodiments, one of the top electrodes 2702 and 2704, one of the piezoelectric layers 2602, 2604 and 2606, and one of the bottom electrodes 2502 may form a two-terminal piezoelectric element and may vibrate when an electrical potential is applied across the top and bottom electrodes.

Figure 28:
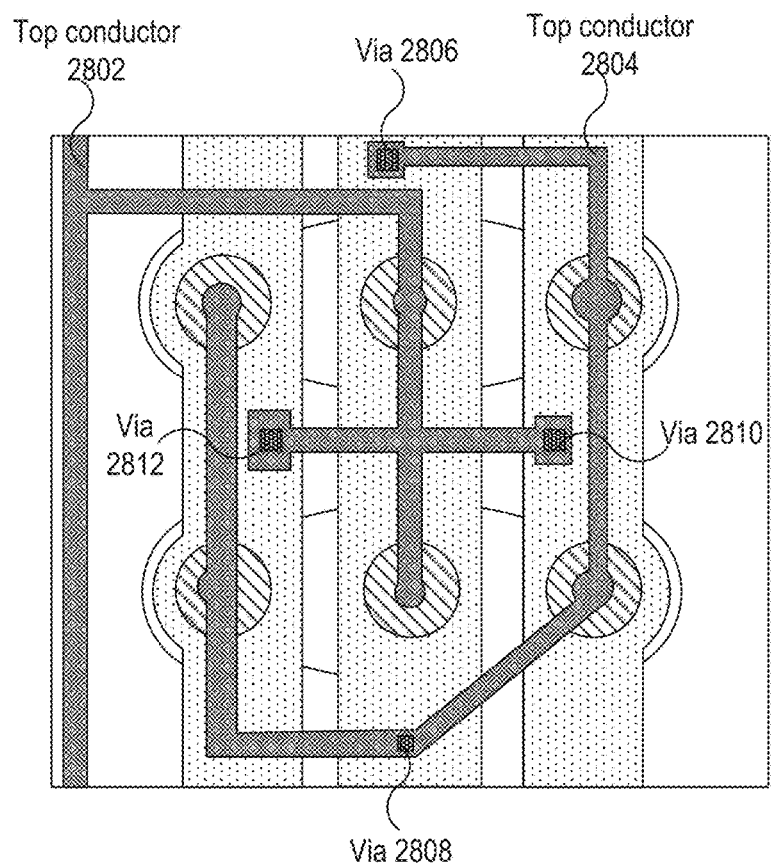

FIG. 28 shows top conductors 2802 and 2804 that are electrically connected to the top electrodes 2702 and 2704 according to embodiments of the present disclosure. The top conductor 2802 may be electrically connected to the two top electrodes 2704 while the top conductor 2804 may be electrically connected to the four top electrodes 2702. In embodiments, the top electrodes may be electrically connected to the bottom conductors 2504a and 2504b through vias. For instance, the vias 2806 and 2808 may electrically connect the four top electrodes 2702 to the bottom conductor 2504 while the vias 2810 and 2812 may electrically connect the two top electrodes 2704 to the bottom conductors 2504b and 2504c.

Figure 29:
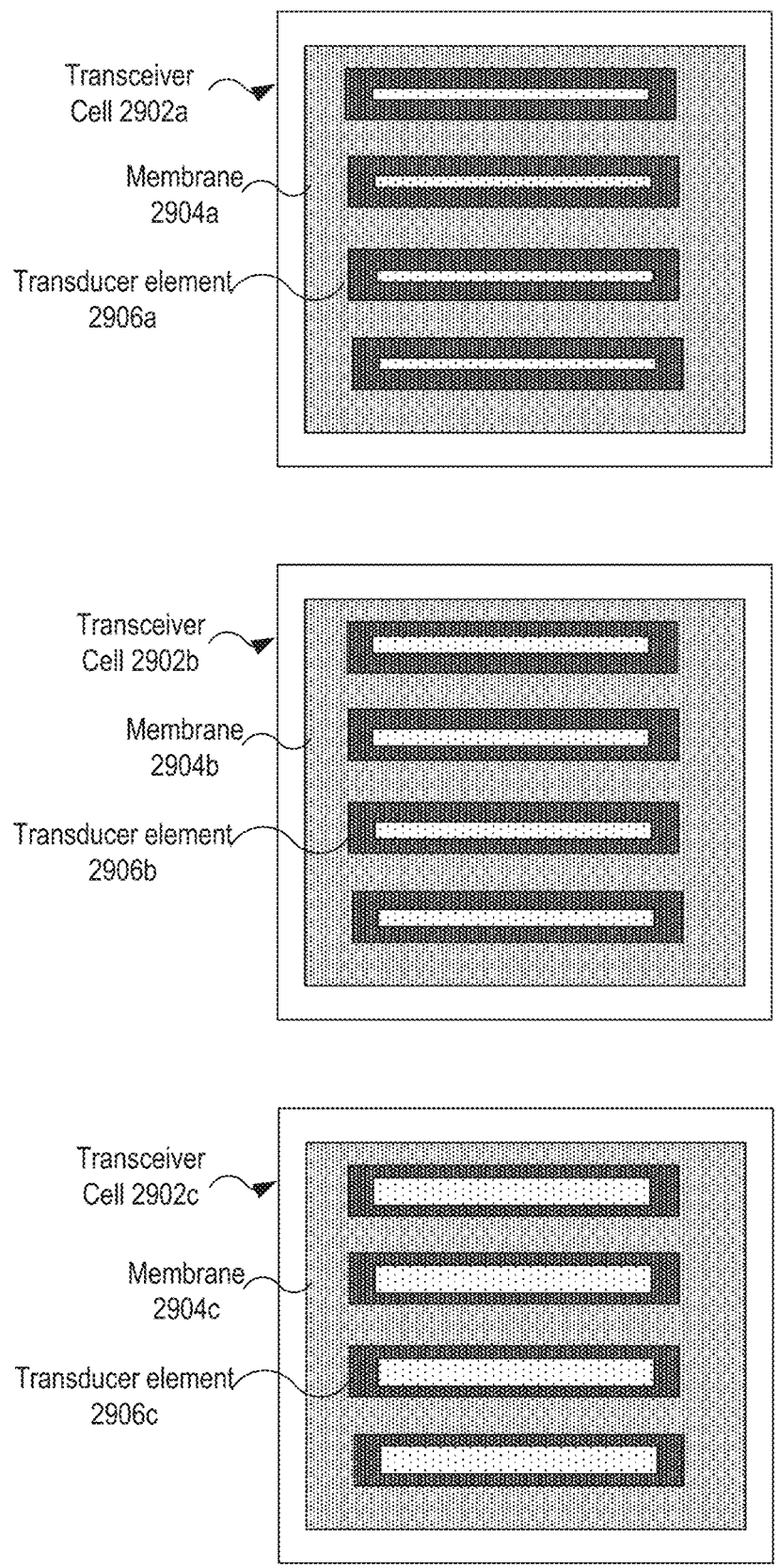
FIG. 29 shows a schematic diagram of three transceiver cells having different electrode patterns according to embodiments of the present disclosure.

FIG. 29 shows a schematic diagram of three transceiver cells 2902a-2902c having different electrode patterns according to embodiments of the present disclosure. As depicted, each transceiver cell (e.g., 2902a) may have one membrane (e.g., 2904a) and four transducer elements (e.g., 2906a) disposed on the membrane. In embodiments, the gain of each transceiver cell may be a function of various factors: size, shape, and number of the transducer elements, size and shape of the top electrode of each transducer element, size and shape of each membrane, spacing between the transducer elements, polarization of each transducer element, so on.

Figure 30:
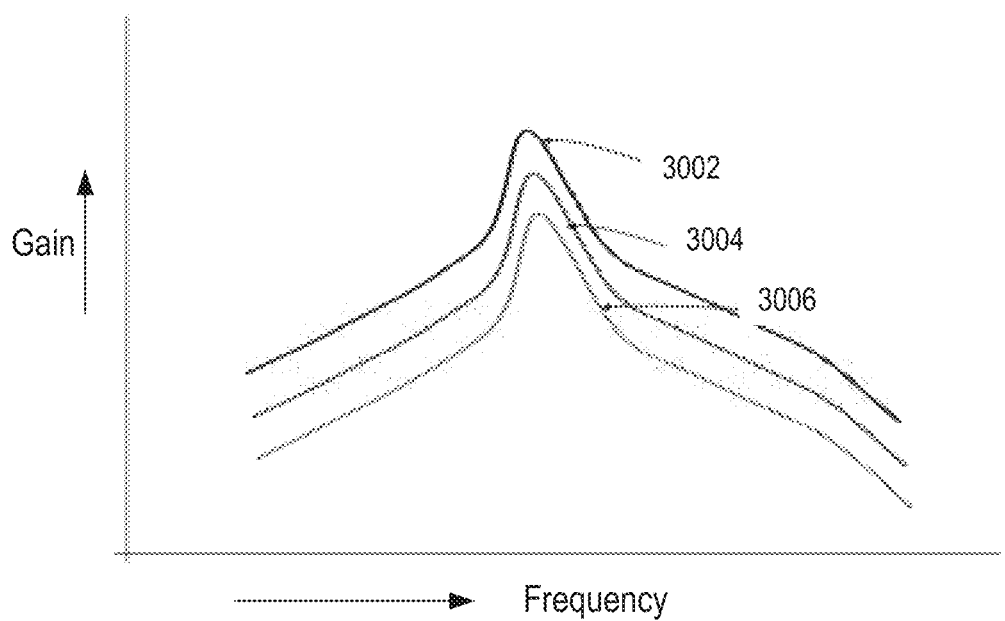
FIG. 30 shows a plot of gains of the transceiver cells in FIG. 29 as a function of frequency according to embodiments of the present disclosure.

For the purpose of illustration, in FIG. 29, the projection area of the top electrode is changed to control the gain of the transducer cell. In embodiments, the top electrodes of the transducer elements 2904c is larger than the top electrodes of the transducer elements 2904b, and the top electrodes of the transducer elements 2904b is larger than the top electrodes of the transducer elements 2904a. While the other factors that affect the gain, such as size and number of transducer elements 2906a-2906c and size of the membranes 2904a-2904c, are the same in the transceiver cells 2902a-2902c, the gain of the transceiver cells 2902a-2902c varies depending on the size of the top electrode. FIG. 30 illustrates a plot of gains of the transceiver cells 2902a-2902c as a function of frequency, where the curves 3002, 3004, and 3006 may correspond to the transceiver elements 2902a-2902c, respectively. As depicted, the gain of the transceiver cells decreases as the size of the top electrodes increases.

It should be apparent to those of ordinary skill in the art that, in embodiments: (i) each of the transceiver arrays, tiles, cells membranes, piezoelectric elements, and electrodes of a piezoelectric elements may have any suitable shape; (ii) the placement of tiles in a transceiver array, the placement of cells in a tile, the placement of membranes in a cell, the placement of piezoelectric elements on a membrane, and the placement of electrodes on the piezoelectric element, and the placement of capacitor pads may be arbitrary; (iii) the variation of the thickness of a membrane may be changed arbitrarily to enhance or change the performance of the membrane; (iv) the number of tiles in a transceiver array, the number of cells in a tile, the number of membranes in a cell, and the number of piezoelectric elements in a membrane can be varied by design; (v) the polarization of the piezoelectric elements may be varied during the operation of the device; (vi) the components in a transceiver array may be combined in a beneficial manner; (vii) the placement of perforations in a membrane that allows transmission of laser light may be arbitrary; and (viii) the interlayer dielectrics, electrical vias, electrical redistribution layers, acoustic impedance matching layers, moisture protection barriers, housings, and electrical interconnections may be formed of materials that are typically used in the semiconductor, MEMS, or ultrasound industries.

While the invention is susceptible to various modifications and alternative forms, specific examples thereof have been shown in the drawings and are herein described in detail. It should be understood, however, that the invention is not to be limited to the particular forms disclosed, but to the contrary, the invention is to cover all modifications, equivalents, and alternatives falling within the scope of the appended claims.

What is claimed is:

1. A transceiver element, comprising:
   a substrate;
   a membrane suspending from the substrate; and a transducer element mounted on the at least one membrane at an attachment area, the transducer element having a bottom electrode, a piezoelectric layer on the bottom electrode, and at least one top electrode on the piezoelectric layer, the transducer element generating a bending moment in response to applying an electrical potential across the bottom electrode and the at least one top electrode and developing an electrical charge in response to applying a bending moment thereto;

wherein the membrane has a first cross-sectional thickness in the attachment area and a second cross-sectional thickness in a deflection area of the membrane, the first cross-sectional thickness being different from the second cross-sectional thickness to permit a desired deflection profile of the membrane for enhancing sensitivity of the transducer element.

2. The transceiver element of claim 1, wherein the piezoelectric layer of a first transducer element of the transducer element is polarized in a direction opposite to the piezoelectric layer of a second transducer element.

3. The transceiver element of claim 1, further comprising a second substrate, wherein the second substrate includes a first metal conductor and the membrane includes a second metal conductor and wherein the first and second metal conductors form a capacitor.

4. The transceiver element of claim 1, further comprising a second substrate, wherein the second substrate includes a light source and the membrane includes an aperture that is arranged to pass a portion of light emitted by the light source.

5. The transceiver element of claim 1, wherein the membrane includes a bump to thereby create an increase in the cross-sectional thickness of the membrane.

6. The transceiver element of claim 1, wherein the cross-sectional thickness of the membrane creates stress shaping regions to deflect the membrane in a predetermined manner when a bending moment is applied thereto.

7. The transceiver element of claim 1, wherein the membrane comprises a plurality of membranes, and further comprising one or more grooves formed in the substrate and disposed between adjacent membranes, wherein the one or more grooves attenuate acoustic cross-talk between the transducer element and a second transducer element.

8. The transceiver element of claim 1, comprising first and second transducer elements configured to generate bending moments in opposite directions.

9. The transceiver element of claim 1, wherein the at least one top electrode of a first transducer element is electrically coupled to the bottom electrode of a second transducer element and wherein the bottom electrode of the first transducer element is electrically coupled to the at least one top electrode of the second transducer element.

10. The transceiver element of claim 1, wherein the piezoelectric layer includes one or more piezoelectric sublayers.

11. The transceiver element of claim 1, wherein the membrane includes first and second membranes and the first and second membranes are actuated at different modes of resonance.

12. The transceiver element of claim 1, wherein an electrical signal applied to a first piezoelectric element has a phase delay relative to an electrical signal applied to a second piezoelectric element.

13. The transceiver element of claim 1, wherein the membrane includes first and second membranes and the first membrane operates in a transmission mode to generate a pressure wave and the second membrane operates only in a receive mode to detect a pressure wave.

14. The transceiver element of claim 1, wherein the substrate includes at least one cavity that is disposed below the membrane and wherein the cavity is in vacuum or filled with a gas.

15. An imaging system, comprising:
a transceiver cell for generating a pressure wave and converting an external pressure wave into an electrical signal; and
a control unit for controlling an operation of the transceiver cell,
the transceiver cell including:
a substrate;
at least one membrane suspending from the substrate;
at least one groove cut into the at least one membrane; and
a plurality of transducer elements mounted on the at least one membrane, each of the plurality of transducer elements having a bottom electrode, a piezoelectric layer on the bottom electrode, and at least one top electrode on the piezoelectric layer, each of the plurality of transducer elements generating a bending moment in response to applying an electrical potential across the bottom electrode and the at least one top electrode and developing an electrical charge in response to applying a bending moment thereto wherein the at least one groove defines an area of lesser membrane thickness for permitting a desired deflection profile of the membrane for enhancing sensitivity of the transducer elements.

16. The imaging system of claim 15, further comprising:
a coating layer for focusing the pressure wave generated by the transceiver cell.

17. The imaging system of claim 15, further comprising:
a processor for processing the electrical signal; and
a display for displaying an image based on a processed signal from the processor.

18. The imaging system of claim 15, wherein the piezoelectric layer of a first transducer element of the plurality of transducer elements is polarized in a direction opposite to the piezoelectric layer of a second transducer element of the plurality of transducer elements.

19. The imaging system of claim 15, wherein the at least one membrane includes first and second membranes and the first and second membranes are actuated at different modes of resonance.

20. The imaging system of claim 15, wherein the control unit comprises an application-specific integrated circuit (ASIC) chip.

21. A transceiver element, comprising:
a substrate that defines a cavity;
at least one membrane suspending from the substrate above the cavity; and
a plurality of transducer elements mounted on the at least one membrane, each of the plurality of transducer elements having a bottom electrode, a piezoelectric layer on the bottom electrode, and at least one top electrode on the piezoelectric layer, each of the plurality of transducer elements generating a bending moment in response to applying an electrical potential across the bottom electrode and the at least one top electrode and developing an electrical charge in response to applying a bending moment thereto,
wherein a first transducer element of the plurality of transducer elements is surrounded by a second transducer element of the plurality of transducer elements, and wherein the at least one membrane, when seen in a side cross-sectional view, has a thickness that varies based on the presence of a groove, corrugation, perforation, aperture, or bump in or on the at least one membrane, wherein the thickness of the membrane permits a piston motion to be generated when one or more electrical fields are applied to the first and second transducer elements on the at least one membrane.

22. The transceiver element of claim 21, wherein the first transducer element has a rectangular shape with rounded corners and the second transducer element has a shape of a belt surrounding the first transducer element.

23. The transceiver element of claim 21, wherein the at least one membrane includes one or more grooves to thereby have a variance in the thickness.

24. The transceiver element of claim 21, wherein the substrate includes at least one cavity that is disposed below the at least one membrane and wherein the cavity is in vacuum or filled with a gas.

25. The transceiver element of claim 21, wherein the piezoelectric layer of the first transducer element of the plurality of transducer elements is polarized in a direction opposite to the piezoelectric layer of the second transducer element of the plurality of transducer elements.

26. The transceiver element of claim 21, wherein the first and second transducer elements generate bending moments in opposite directions.

27. The transceiver element of claim 21, wherein the first transducer element generates a bending moment in a same direction as the second transducer element.

28. The transceiver element of claim 21, wherein the at least one membrane includes first and second membranes and the first membrane operates in a transmission mode to generate a pressure wave and the second membrane operates only in a receive mode to detect a pressure wave.

29. The transceiver element of claim 21, wherein the piezoelectric layer includes at least one of PZT, KNN, PZT-N, PMN-Pt, AlN, Sc—AlN, ZnO, PVDF, and LiNiO$_3$.

30. The transceiver element of claim 1, further comprising at least one additional transducer element mounted on the membrane.

31. The transceiver element of claim 1, wherein membrane comprises first and second sides, a first groove extending from the first side into the membrane, and a second groove extending from the second side into the membrane.

32. The transceiver element of claim 1, wherein membrane comprises first and second grooves extending into the membrane, the first groove having a cross-sectional profile different from a cross-sectional profile of the second groove.

33. A transceiver element, comprising:
a substrate that defines a cavity;
a membrane coupled to the substrate and suspended above the cavity; and
a piezoelectric element mounted on the membrane,
wherein the membrane, when seen in a side cross-sectional view, has a thickness that varies based on the presence of a groove, corrugation, perforation, aperture, or bump in or on the membrane for permitting a desired membrane deflection profile for enhancing sensitivity of the piezoelectric element.

34. The transceiver element of claim 33, wherein membrane comprises first and second sides, a first groove extending from the first side into the membrane, and a second groove extending from the second side into the membrane.

35. The transceiver element of claim 33, wherein the first piezoelectric element is surrounded by the first groove.

36. The transceiver element of claim 33, further comprising a second piezoelectric element surrounding the first piezoelectric element.

37. The transceiver element of claim 33, further comprising a second groove located next to the first groove.

38. The transceiver element of claim 33, wherein the first and second grooves have different widths.

39. The transceiver element of claim 33, wherein the first and second grooves have different depths.

* * * * *